US009836580B2

(12) United States Patent
Fendell et al.

(10) Patent No.: US 9,836,580 B2
(45) Date of Patent: Dec. 5, 2017

(54) PROVIDER PORTAL

(71) Applicant: Palantir Technologies, Inc., Palo Alto, CA (US)

(72) Inventors: Sam Fendell, Palo Alto, CA (US); James Thompson, San Francisco, CA (US)

(73) Assignee: Palantir Technologies Inc., Palo Alto, CA (US)

( * ) Notice: Subject to any disclaimer, the term of this patent is extended or adjusted under 35 U.S.C. 154(b) by 101 days.

(21) Appl. No.: 14/222,364

(22) Filed: Mar. 21, 2014

(65) Prior Publication Data
US 2015/0269334 A1 Sep. 24, 2015

(51) Int. Cl.
*G06F 19/00* (2011.01)
*G06Q 40/08* (2012.01)
*G06Q 50/24* (2012.01)
*G06Q 50/22* (2012.01)

(52) U.S. Cl.
CPC .......... *G06F 19/328* (2013.01); *G06F 19/322* (2013.01); *G06Q 40/08* (2013.01); *G06Q 50/22* (2013.01); *G06Q 50/24* (2013.01)

(58) Field of Classification Search
CPC ........ G06Q 50/22; G06Q 50/24; G06Q 40/08; G06F 19/328; G06F 19/322
USPC ................................ 705/2, 3, 4, 30; 707/754
See application file for complete search history.

(56) References Cited

U.S. PATENT DOCUMENTS

| | | |
|---|---|---|
| 5,670,987 A | 9/1997 | Doi et al. |
| 6,161,098 A | 12/2000 | Wallman |
| 6,219,053 B1 | 4/2001 | Tachibana et al. |
| 6,232,971 B1 * | 5/2001 | Haynes ................. G06F 9/4443 715/800 |
| 6,279,018 B1 | 8/2001 | Kudrolli et al. |
| 6,341,310 B1 | 1/2002 | Leshem et al. |
| 6,369,835 B1 | 4/2002 | Lin |
| 6,523,019 B1 | 2/2003 | Borthwick |
| 6,549,944 B1 | 4/2003 | Weinberg et al. |
| 6,714,936 B1 | 3/2004 | Nevin, III |
| 6,839,745 B1 | 1/2005 | Dingari et al. |

(Continued)

FOREIGN PATENT DOCUMENTS

| | | | |
|---|---|---|---|
| WO | WO 2009/061501 | 5/2009 | |
| WO | WO 2010/030913 | 3/2010 | |
| WO | WO 2010/030913 A2 * | 3/2010 | ............... G06F 9/06 |

OTHER PUBLICATIONS

"A First Look: Predicting Market Demand for Food Retail using a Huff Analysis," TRF Policy Solutions, Jul. 2012, pp. 30.

(Continued)

*Primary Examiner* — Barbara Joan Amelunxen
(74) *Attorney, Agent, or Firm* — Knobbe Martens Olson & Bear LLP

(57) ABSTRACT

Various systems and methods are provided that graphically allow health insurance company personnel to identify patient diagnoses that are not accounted for by the health insurance company. Furthermore, the various systems and methods graphically allow health insurance company personnel to identify patients that have not submitted claims for documented ailments or conditions. Thus, the health insurance company may be able to improve its chances of receiving transfer payments from other health insurance companies and/or receiving higher star ratings.

19 Claims, 23 Drawing Sheets

(56) References Cited

U.S. PATENT DOCUMENTS

| | | |
|---|---|---|
| 6,978,419 B1 | 12/2005 | Kantrowitz |
| 7,139,800 B2 | 11/2006 | Bellotti et al. |
| 7,171,427 B2 | 1/2007 | Witkowski et al. |
| 7,278,105 B1 | 10/2007 | Kitts |
| 7,379,903 B2 | 5/2008 | Joseph |
| 7,426,654 B2 | 9/2008 | Adams et al. |
| 7,454,466 B2 | 11/2008 | Bellotti et al. |
| 7,467,375 B2 | 12/2008 | Tondreau et al. |
| 7,525,422 B2 | 4/2009 | Bishop et al. |
| 7,617,232 B2 | 11/2009 | Gabbert et al. |
| 7,627,812 B2 | 12/2009 | Chamberlain et al. |
| 7,634,717 B2 | 12/2009 | Chamberlain et al. |
| 7,703,021 B1 | 4/2010 | Flam |
| 7,716,077 B1 | 5/2010 | Mikurak |
| 7,725,547 B2 | 5/2010 | Albertson et al. |
| 7,765,489 B1* | 7/2010 | Shah ................. G06Q 10/107 715/210 |
| 7,770,100 B2 | 8/2010 | Chamberlain et al. |
| 7,818,658 B2 | 10/2010 | Chen |
| 7,877,421 B2 | 1/2011 | Berger et al. |
| 7,962,848 B2 | 6/2011 | Bertram |
| 7,966,199 B1* | 6/2011 | Frasher ............... G06Q 10/10 701/532 |
| 8,001,465 B2 | 8/2011 | Kudrolli et al. |
| 8,001,482 B2 | 8/2011 | Bhattiprolu et al. |
| 8,015,487 B2 | 9/2011 | Roy et al. |
| 8,036,971 B2 | 10/2011 | Aymeloglu et al. |
| 8,225,201 B2 | 7/2012 | Michael |
| 8,230,333 B2 | 7/2012 | Decherd et al. |
| 8,447,722 B1 | 5/2013 | Ahuja et al. |
| 8,489,641 B1 | 7/2013 | Seefeld et al. |
| 8,514,082 B2 | 8/2013 | Cova et al. |
| 8,554,579 B2 | 10/2013 | Tribble et al. |
| 8,577,911 B1 | 11/2013 | Stepinski et al. |
| 8,620,641 B2 | 12/2013 | Farnsworth et al. |
| 8,682,696 B1* | 3/2014 | Shanmugam ......... G06Q 10/10 705/35 |
| 8,689,108 B1 | 4/2014 | Duffield et al. |
| 8,713,467 B1 | 4/2014 | Goldenberg et al. |
| 8,799,313 B2* | 8/2014 | Satlow ................ G06F 19/328 707/705 |
| 2001/0021936 A1 | 9/2001 | Bertram |
| 2002/0130907 A1 | 9/2002 | Chi et al. |
| 2002/0147805 A1 | 10/2002 | Leshem et al. |
| 2002/0174201 A1 | 11/2002 | Ramer et al. |
| 2003/0036927 A1* | 2/2003 | Bowen ................. G06F 19/322 705/4 |
| 2003/0200217 A1 | 10/2003 | Ackerman |
| 2004/0085318 A1 | 5/2004 | Hassler et al. |
| 2004/0095349 A1 | 5/2004 | Bito et al. |
| 2004/0181554 A1 | 9/2004 | Heckerman et al. |
| 2005/0028094 A1* | 2/2005 | Allyn .................. G06F 3/0481 715/273 |
| 2005/0125715 A1* | 6/2005 | Di Franco ............ G06F 17/243 715/226 |
| 2005/0180330 A1 | 8/2005 | Shapiro |
| 2006/0026170 A1 | 2/2006 | Kreitler et al. |
| 2006/0045470 A1 | 3/2006 | Poslinski et al. |
| 2006/0074866 A1 | 4/2006 | Chamberlain et al. |
| 2006/0080139 A1* | 4/2006 | Mainzer .............. G06Q 30/02 705/2 |
| 2006/0080619 A1 | 4/2006 | Carlson et al. |
| 2006/0129746 A1* | 6/2006 | Porter ................. G06F 9/4443 711/100 |
| 2006/0178915 A1* | 8/2006 | Chao ................. G06F 19/3443 705/4 |
| 2007/0011304 A1 | 1/2007 | Error |
| 2007/0136095 A1* | 6/2007 | Weinstein ........... G06F 19/3418 705/2 |
| 2007/0266336 A1 | 11/2007 | Nojima et al. |
| 2007/0299697 A1 | 12/2007 | Friedlander et al. |
| 2008/0069081 A1 | 3/2008 | Chand et al. |
| 2008/0077597 A1 | 3/2008 | Butler |
| 2008/0077642 A1 | 3/2008 | Carbone et al. |
| 2008/0249820 A1* | 10/2008 | Pathria ................ G06Q 10/10 705/2 |
| 2008/0263468 A1 | 10/2008 | Cappione et al. |
| 2008/0270438 A1* | 10/2008 | Aronson ............. G06F 19/322 |
| 2009/0043801 A1* | 2/2009 | LeClair ............... G06Q 40/08 |
| 2009/0076845 A1 | 3/2009 | Bellin et al. |
| 2009/0094166 A1 | 4/2009 | Aymeloglu et al. |
| 2009/0132953 A1 | 5/2009 | Reed et al. |
| 2009/0164934 A1 | 6/2009 | Bhattiprolu et al. |
| 2009/0177492 A1* | 7/2009 | Hasan ................. G06F 19/322 705/3 |
| 2009/0187548 A1 | 7/2009 | Ji et al. |
| 2009/0198518 A1* | 8/2009 | McKenzie .......... G06Q 10/087 705/3 |
| 2009/0222287 A1* | 9/2009 | Legorreta ............ G06Q 10/10 705/3 |
| 2009/0281839 A1* | 11/2009 | Lynn ................. G06F 19/321 705/3 |
| 2009/0287470 A1 | 11/2009 | Farnsworth et al. |
| 2010/0070897 A1 | 3/2010 | Aymeloglu et al. |
| 2010/0082369 A1* | 4/2010 | Prenelus ............. G06F 19/322 705/3 |
| 2010/0122152 A1 | 5/2010 | Chamberlain et al. |
| 2010/0280851 A1* | 11/2010 | Merkin ............... G06F 19/322 705/3 |
| 2010/0293174 A1 | 11/2010 | Bennett et al. |
| 2010/0306713 A1 | 12/2010 | Geisner et al. |
| 2010/0325581 A1 | 12/2010 | Finkelstein et al. |
| 2011/0047159 A1 | 2/2011 | Baid et al. |
| 2011/0060753 A1 | 3/2011 | Shaked et al. |
| 2011/0161409 A1* | 6/2011 | Nair .................... G06F 8/38 709/203 |
| 2011/0167105 A1 | 7/2011 | Ramakrishnan et al. |
| 2011/0179048 A1* | 7/2011 | Satlow ................ G06F 19/328 707/754 |
| 2011/0208724 A1 | 8/2011 | Jones et al. |
| 2011/0291851 A1 | 12/2011 | Whisenant |
| 2011/0310005 A1 | 12/2011 | Chen et al. |
| 2012/0004894 A1* | 1/2012 | Butler ................. G06F 19/322 703/11 |
| 2012/0019559 A1 | 1/2012 | Siler et al. |
| 2012/0036434 A1 | 2/2012 | Oberstein |
| 2012/0066166 A1 | 3/2012 | Curbera et al. |
| 2012/0084184 A1* | 4/2012 | Raleigh ............. H04M 15/7652 705/30 |
| 2012/0144335 A1 | 6/2012 | Abeln et al. |
| 2012/0196558 A1 | 8/2012 | Reich et al. |
| 2012/0197657 A1* | 8/2012 | Prodanovic .......... G06Q 50/22 705/2 |
| 2012/0197660 A1* | 8/2012 | Prodanovich ........ G06Q 30/04 705/2 |
| 2012/0221580 A1 | 8/2012 | Barney |
| 2012/0246148 A1 | 9/2012 | Dror |
| 2012/0323888 A1 | 12/2012 | Osann, Jr. |
| 2012/0330973 A1 | 12/2012 | Ghuneim et al. |
| 2013/0006668 A1 | 1/2013 | Van Arkel et al. |
| 2013/0046842 A1 | 2/2013 | Muntz et al. |
| 2013/0061169 A1 | 3/2013 | Pearcy et al. |
| 2013/0073377 A1 | 3/2013 | Heath |
| 2013/0097482 A1 | 4/2013 | Marantz et al. |
| 2013/0224696 A1 | 8/2013 | Wolfe et al. |
| 2013/0262527 A1 | 10/2013 | Hunter et al. |
| 2013/0290011 A1 | 10/2013 | Lynn et al. |
| 2013/0290825 A1 | 10/2013 | Arndt et al. |
| 2014/0012796 A1 | 1/2014 | Petersen et al. |
| 2014/0019936 A1 | 1/2014 | Cohanoff |
| 2014/0032506 A1 | 1/2014 | Hoey et al. |
| 2014/0033010 A1 | 1/2014 | Richardt et al. |
| 2014/0244284 A1* | 8/2014 | Smith ................. G06F 19/328 705/2 |
| 2015/0269316 A1* | 9/2015 | Hussam .............. G06Q 50/24 705/3 |

OTHER PUBLICATIONS

Acklen, Laura, "Absolute Beginner's Guide to Microsoft Word 2003," Dec. 24, 2003, pp. 15-18, 34-41, 308-316.

(56) References Cited

OTHER PUBLICATIONS

Ananiev et al., "The New Modality API," http://web.archive.org/web/20061211011958/http://java.sun.com/developer/technicalArticles/J2SE/Desktop/javase6/modality/ Jan. 21, 2006, pp. 8.

Appacts, "Smart Thinking for Super Apps," http://www.appacts.com printed Jul. 18, 2013 in 4 pages.

Apsalar, "Data Powered Mobile Advertising," "Free Mobile App Analytics" and various analytics related screen shots http://apsalar.com Printed Jul. 18, 2013 in 8 pages.

Bugzilla@Mozilla, "Bug 18726—[feature] Long-click means of invoking contextual menus not supported," http://bugzilla.mozilla.org/show_bug.cgi?id=18726 printed Jun. 13, 2013 in 11 pages.

Capptain—Pilot Your Apps, http://www.capptain.com Printed Jul. 18, 2013 in 6 pages.

Chen et al., "Bringing Order to the Web: Automatically Categorizing Search Results," CHI 2000, Proceedings of the SIGCHI conference on Human Factors in Computing Systems, Apr. 1-6, 2000, The Hague, The Netherlands, pp. 145-152.

Countly Mobile Analytics, http://count.ly/ Printed Jul. 18, 2013 in 9 pages.

Distimo—App Analytics, http://www.distimo.com/app-analytics Printed Jul. 18, 2013 in 5 pages.

Dramowicz, Ela, "Retail Trade Area Analysis Using the Huff Model," Directions Magazine, Jul. 2, 2005 in 10 pages, http://www.directionsmag.com/articles/retail-trade-area-analysis-using-the-huff-model/123411.

Flurry Analytics, http://www.flurry.com/ Printed Jul. 18, 2013 in 14 pages.

GIS-Net 3 Public—Department of Regional Planning. Planning & Zoning Information for Unincorporated LA County. Retrieved Oct. 2, 2013 from http://gis.planning.lacounty.gov/GIS-NET3_Public/Viewer.html.

Google Analytics Official Website—Web Analytics & Reporting, http://www.google.com/analytics.index.html Printed Jul. 18, 2013 in 22 pages.

Griffith, Daniel A., "A Generalized Huff Model," Geographical Analysis, Apr. 1982, vol. 14, No. 2, pp. 135-144.

Hibbert et al., "Prediction of Shopping Behavior Using a Huff Model Within a GIS Framework," Healthy Eating in Context Mar. 18, 2011, pp. 16.

Huff et al., "Calibrating the Huff Model Using ArcGIS Business Analyst," ESRI, Sep. 2008, pp. 33.

Huff, David L., "Parameter Estimation in the Huff Model," ESRI, ArcUser, Oct.-Dec. 2003, pp. 34-36.

Keylines.com, "An Introduction to KeyLines and Network Visualization," Mar. 2014, http://keylines.com/wp-content/uploads/2014/03/KeyLines-White-Paper.pdf downloaded May 12, 2014 in 8 pages.

Keylines.com, "KeyLines Datasheet," Mar. 2014, http://keylines.com/wp-content/uploads/2014/03/KeyLines-datasheet.pdf downloaded May 12, 2014 in 2 pages.

Keylines.com, "Visualizing Threats: Improved Cyber Security Through Network Visualization," Apr. 2014, http://keylines.com/wp-content/uploads/2014/04/Visualizing-Threats1.pdf downloaded May 12, 2014 in 10 pages.

Kontagent Mobile Analytics, http://www.kontagent.com/ Printed Jul. 18, 2013 in 9 pages.

Liu, Tianshun, "Combining GIS and the Huff Model to Analyze Suitable Locations for a New Asian Supermarket in the Minneapolis and St. Paul, Minnesota USA," Papers in Resource Analysis, 2012, vol. 14, pp. 8.

Localytics—Mobile App Marketing & Analytics, http://www.localytics.com/ Printed Jul. 18, 2013 in 12 pages.

Manske, "File Saving Dialogs," http://www.mozilla.org/editor/ui_specs/FileSaveDialogs.html, Jan. 20, 1999, pp. 7.

Map of San Jose, CA. Retrieved Oct. 2, 2013 from http://maps.bing.com.

Map of San Jose, CA. Retrieved Oct. 2, 2013 from http://maps.google.com.

Map of San Jose, CA. Retrieved Oct. 2, 2013 from http://maps.yahoo.com.

Microsoft—Developer Network, "Getting Started with VBA in Word 2010," Apr. 2010, http://msdn.microsoft.com/en-us/library/ff604039%28v=office.14%29.aspx printed Apr. 4, 2014 in 17 pages.

Microsoft Office—Visio, "About connecting shapes," http://office.microsoft.com/en-us/visio-help/about-connecting-shapes-HP085050369.aspx printed Aug. 4, 2011 in 6 pages.

Microsoft Office—Visio, "Add and glue connectors with the Connector tool," http://office.microsoft.com/en-us/visio-help/add-and-glue-connectors-with-the-connector-tool-HA010048532.aspx?CTT=1 printed Aug. 4, 2011 in 1 page.

Mixpanel—Mobile Analytics, https://mixpanel.com/ Printed Jul. 18, 2013 in 13 pages.

Official Communication in New Zealand Application No. 624557 dated May 14, 2014.

Open Web Analytics (OWA), http://www.openwebanalytics.com/ Printed Jul. 19, 2013 in 5 pages.

Piwik—Free Web Analytics Software. http://piwik.org/ Printed Jul. 19, 2013 in 18 pages.

StatCounter—Free Invisible Web Tracker, Hit Counter and Web Stats, http://statcounter.com/ Printed Jul. 19, 2013 in 17 pages.

TestFlight—Beta Testing on the Fly, http://testflightapp.com/ Printed Jul. 18, 2013 in 3 pages.

trak.io, http://trak.io/ printed Jul. 18, 2013 in 3 pages.

UserMetrix, http://usermetrix.com/android-analytics printed Jul. 18, 2013 in 3 pages.

* cited by examiner

CHECKLIST 210

TASKS

Inbox 215 164

Archived

PROVIDERS 217 Sort ▼

Provider 218A
Provider 218B
Provider 218C
Provider 218D
Provider 218E
Provider 218F
Provider 218G
Provider 218H
Provider 218I
Provider 218J
Provider 218K
Provider 218L 240 242 244

220 212 222 230

| CLAIMS ADJUSTMENTS | 27 | GAPS IN CARE | 116 | Sort ▼ |

27 NEW CLAIMS TO ADJUST ASSOCIATED WITH PROVIDER 218A

☐ Patient #200016382 — Claim #155385 (2013-09-22) is missing asthma or COPD diagnosis. Member has asthma or COPD prescriptions in 2013 but no related diagnosis.

☐ Patient #200010065 — Claim #95423 (2013-10-16) is missing diabetes diagnosis. Member has diabetes prescriptions in 2013 but no related diagnosis.

☐ Patient #200047720 — Claim #453087 (2013-12-16) is missing diabetes diagnosis. Member has diabetes prescriptions in 2013 but no related diagnosis.

☐ Patient #200004994 — Claim #47223 (2013-08-15) is missing diabetes diagnosis. Member has diabetes prescriptions in 2013 but no related diagnosis.

☐ Patient #200002060 — Claim #19426 (2013-11-08) is missing diabetes diagnosis. Member has diabetes prescriptions in 2013 but no related diagnosis.

☐ Patient #200039938 — Claim #379115 (2013-02-04) is missing diabetes diagnosis. Member has diabetes prescriptions in 2013 but no related diagnosis.

☐ Patient #200030296 — Claim #287571 (2013-09-22) is missing diabetes diagnosis. Member has diabetes prescriptions in 2013 but no related diagnosis.

☐ Patient #200043828 — Claim #416233 (2013-10-16) is missing diabetes diagnosis. Member has diabetes prescriptions in 2013 but no related diagnosis.

☐ Patient #200040614 — Claim #385517 (2013-09-30) is missing diabetes diagnosis. Member has diabetes prescriptions in 2013 but no related diagnosis.

☐ Patient #200030643 — Claim #290913 (2013-08-18) is missing cancer diagnosis. Member has cancer prescriptions in 2013 but no related diagnosis.

☐ Patient #200033141 — Claim #314579 (2013-11-08) is missing diabetes diagnosis. Member has diabetes prescriptions in 2013 but no related diagnosis.

☐ Patient #200029575 — Claim #280571 (2013-11-08) is missing diabetes diagnosis. Member has diabetes prescriptions in 2013 but no related diagnosis.

CHECKLIST

TASKS
- Inbox  1644
- Archived

PROVIDERS
- Provider #1
- Provider #2
- Provider #3
- Provider #4
- Provider #5
- Provider #6
- Provider #7
- Provider #8
- Provider #9
- Provider #10
- Provider #11
- Provider #12

| CLAIMS ADJUSTMENTS | 27 | GAPS IN CARE | 116 |

101 NEW ITEMS

- Patient #200010065 — Make appointment for diabetes. — 742-999-2304
- Patient #200047720 — Make appointment for IHD. — 135-096-0017
- Patient #200031034 — appointment for COPD. — 725-290-7404
  - Mark As Complete
  - 187-832-2108

15 APPOINTMENTS SCHEDULED

- Patient #200018380 — 089-378-0037
- Patient #200013998 — 371-029-7860
- Patient #200025421 — Member is due for a colorectal cancer screen. — 743-935-7653
- Patient #200016382 — Make appointment for asthma or COPD. — 125-044-7858
- Patient #200028239 — 877-555-0248

FIG. 5B

CHECKLIST

TASKS
- Inbox   1644
- Archived

PROVIDERS   Sort ▼
- Provider #1
- Provider #2
- Provider #3
- Provider #4
- Provider #5
- Provider #6
- Provider #7
- Provider #8
- Provider #9
- Provider #10
- Provider #11
- Provider #12

Sort ▼

| CLAIMS ADJUSTMENTS | 27 | GAPS IN CARE | 116 |

100 NEW ITEMS

| 3 | Patient #200010065 | Make appointment for diabetes. | 742-999-2304 |
| 2 | Patient #200047720 | Make appointment for IHD. | 135-096-0017 |
| 2 | Patient #200031034 | | 725-290-7404 |

16 APPOINTMENTS SCHEDULED

| 3 | Patient #200018380 | | 089-378-0037 |
| 2 | Patient #200013998 | Member is due for a colorectal cancer screen. | 371-029-7860 |
| 2 | Patient #200025421 | Make appointment for asthma or COPD. | 743-935-7653 |
| 2 | Patient #200016382 | | 125-044-7858 |
| 2 | Patient #200028239 | | 877-555-0248 |
| 2 | Patient #200034596 | Make appointment for COPD. | 187-832-2108 |

FIG. 5D

| CHECKLIST 210 | | | | |
|---|---|---|---|---|
| TASKS | 215 | | 227 | |
| Inbox | 164 | 220 212 222 | 460 430 | |
| Archived | | CLAIMS ADJUSTMENTS \| 27  GAPS IN CARE \| 115 | Sort ▼ | |
| PROVIDERS | 217 Sort ▼ | 101 NEW ITEMS | | |
| Provider #1 | | ▲ Patient #2000110065   Make appointment for diabetes. | 742-999-2304 | 432 |
| Provider #2 | | ▲ Patient #2000477720   Make appointment for IHD. | 135-096-0017 | |
| Provider #3 | | 2 Patient #2000310034   Member is due for a breast cancer screen. | 725-290-7404 | 632A |
| Provider #4 | | 2 Patient #2000310034   Member is due for a colorectal cancer screen. | | 632B |
| Provider #5 | | ▲ Patient #2000345596   Make appointment for COPD. | 187-832-2108 | 462 |
| Provider #6 | | 15 APPOINTMENTS SCHEDULED | | |
| Provider #7 | | 3 Patient #2000183380 | 089-378-0037 | |
| Provider #8 | | 2 Patient #2000139998 | 371-029-7860 | |
| Provider #9 | | ▲ Patient #2000254211   Member is due for a colorectal cancer screen. | 743-935-7653 | |
| Provider #10 | | 2 Patient #2000163822   Make appointment for asthma or COPD. | 125-044-7858 | |
| Provider #11 | | 2 Patient #2000282339 | 877-555-0248 | |
| Provider #12 | | | | |

CHECKLIST 700

TASKS
- Inbox 215 1644
- Archived 217 Sort ▼

PROVIDERS
- Provider #1
- Provider #2
- Provider #3
- Provider #4
- Provider #5
- Provider #6
- Provider #7
- Provider #8
- Provider #9
- Provider #10
- Provider #11
- Provider #12

---

CLAIMS ADJUSTMENTS | 27  GAPS IN CARE | 116  Sort ▼ — 227

101 NEW ITEMS

| | | | |
|---|---|---|---|
| ▲ Patient #200010065 | Make appointment for diabetes. | | 📞 742-999-2304 |
| 2 Patient #200047720 | Make appointment for IHD. | | 📞 135-096-0017 |
| 2 Patient #200031034 | Member is due for a breast cancer screen. | | 📞 725-290-7404 |
| 2 Patient #200031034 | Member is due for a colorectal cancer screen. SCHEDULED | | |
| ▲ Patient #200034596 | Make appointment for COPD. | | 📞 187-832-2108 |

15 APPOINTMENTS SCHEDULED

| | | | |
|---|---|---|---|
| 3 Patient #200018380 | | | 📞 089-378-0037 |
| 2 Patient #200013998 | | | 📞 371-029-7860 |
| ▲ Patient #200031034 | Member is due for a colorectal cancer screen. | | 📞 725-290-7404 |
| ▲ Patient #200016382 | Make appointment for asthma or COPD. | | 📞 125-044-7858 |
| 2 Patient #200028239 | | | 📞 877-555-0248 |

FIG. 7B

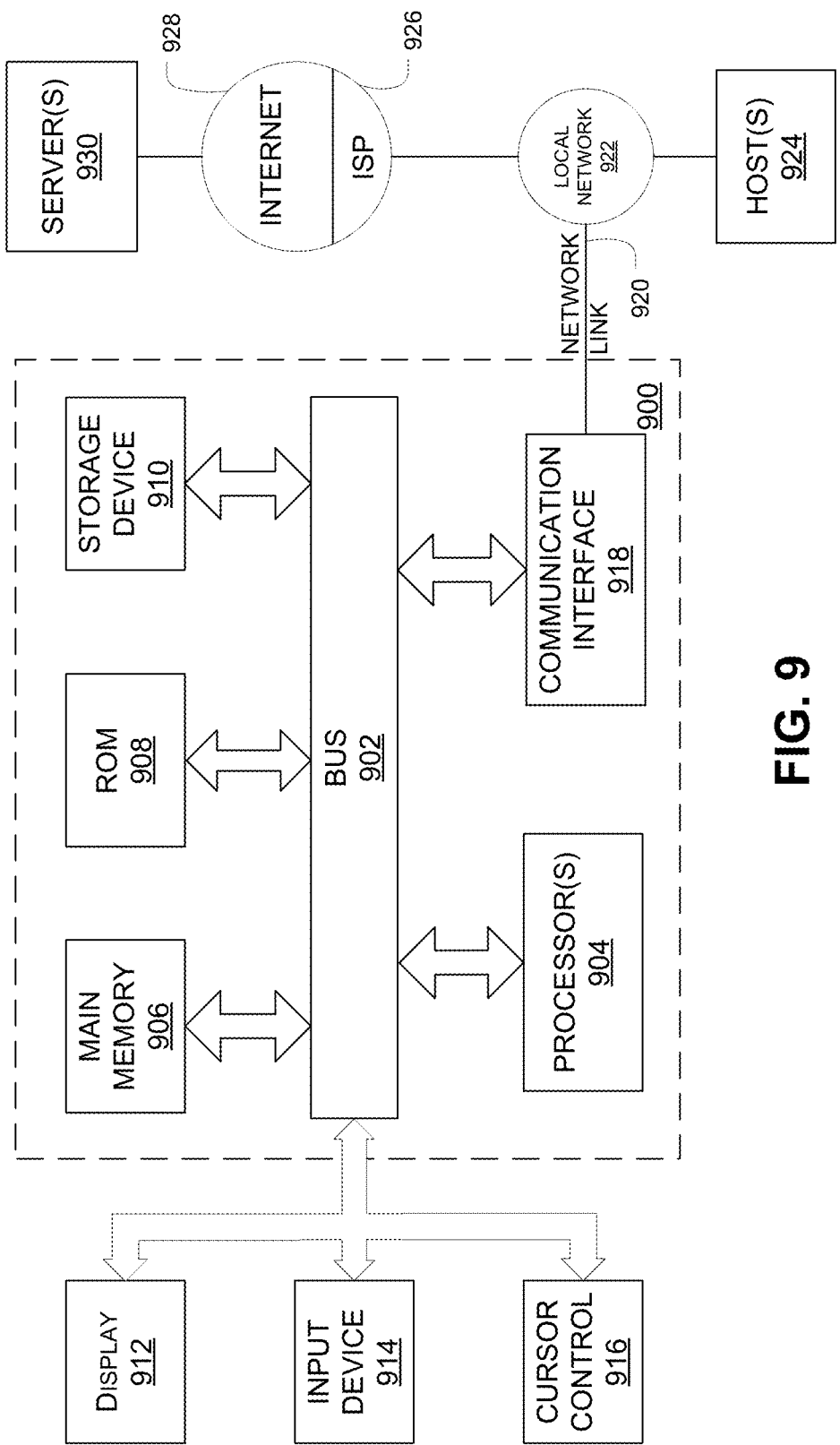

PROVIDER PORTAL

TECHNICAL FIELD

The present disclosure relates to systems and techniques for data integration, analysis, and visualization.

BACKGROUND

Prior to the passing of the Patient Protection and Affordable Care Act (PPACA), insurers were permitted to charge higher premiums for individuals with preexisting conditions (e.g., cancer, heart disease, diabetes, etc.) because such individuals cost the insurer proportionally more in comparison to healthier members. This caused insurance for the sickest and oldest of Americans to be all but unaffordable in many cases. To combat this, individual plans offered via state and federally-administered exchanges are now limited in the scope of conditions that can be used in the pricing of a policy. For example, premiums can be adjusted upwards for individuals who are smokers and/or based on age. However, insurers cannot price the terminal cancer patient out of a policy. The most expensive premium for a given individual on a plan is also capped at three times the cheapest premium on the plan.

However, the fact remains that individuals with preexisting conditions still cost insurers more than healthy individuals. The government, worried that insurers may try to find ways to discriminate against the sickest individuals, implemented a program of risk adjustment. The premise is that insurers that can prove they are insuring a sicker population in comparison to other insurers will be eligible for transfer payments. Thus, insurers with healthier individuals will send money to those with sicker individuals.

In addition, every Medicare Advantage plan offered by insurers is given a rating according to a five-star quality rating system. The whole-number star rating is assigned by virtue of performance across over 50 individual metrics that come from the Healthcare Effectiveness Data and Information Set (HEDIS), the Consumer Assessment of Healthcare Providers and Systems (CAHPS), the Centers for Medicare and Medicaid Services (CMS), the Health Outcomes Survey (HOS), and/or the Independent Review Entity (IRE). The star rating may generally measure the quality of a plan and customer satisfaction with a plan.

Before the PPACA was implemented, insurers received bonus payments based upon the star ratings given to their plans. For example, insurers received a 5% bonus for 5 stars, a 4% bonus for 4 stars, and so forth. Under the PPACA, new performance payments have been added. For example, 4 or 5-star plans will get an additional 1.5% on top of the initial determined amount. These bonus payments increase over time, reaching towards 5% by 2014. Thus, the star rating system has gained more importance under the PPACA.

Over time, insurers can receive claims from healthcare providers. The claims can be used to determine transfer payments and star ratings. However, such a collection may include a large number of claims and/or related data that may be stored in an electronic data store or memory. For example, such a collection of claims may include hundreds of thousands, millions, tens of millions, hundreds of millions, or even billions of claims and/or related data, and may consume significant storage and/or memory. Determination, selection, and analysis of relevant claims and/or related data within such a collection may be extremely difficult for an insurer. Furthermore, processing of such a large collection of claims and/or related data (e.g., as an employee of an insurer uses a computer to sift and/or search through huge numbers of claims and/or related data) may be extremely inefficient and consume significant processing and/or memory resources.

SUMMARY

The systems, methods, and devices described herein each have several aspects, no single one of which is solely responsible for its desirable attributes. Without limiting the scope of this disclosure, several non-limiting features will now be discussed briefly.

Embodiments of the present disclosure relate to the automatic selection of a subset of the received claims and/or related data and to the generation of graphical user interfaces that display the subset. The subset of claims and/or related data may include far fewer claims and/or related data (e.g., several orders of magnitude smaller) than the collection described above. In various embodiments, the graphical user interfaces allow health insurance company personnel to identify patient diagnoses that are not accounted for by the health insurance company. Furthermore, the graphical user interfaces allow health insurance company personnel to identify patients that have not submitted claims for documented ailments or conditions. Accordingly, in an embodiment, processing of the subset of claims and/or related data may be to optimize computing resources as compared to the collection described above. Thus, the health insurance company may be able to improve its chances of receiving transfer payments from other health insurance companies and/or receiving higher star ratings.

One aspect of the disclosure provides a computing system configured to process a large amount of dynamically updating data. The computing system comprises a network interface coupled to a data network for receiving and transmitting one or more packet flows. The computing system further comprises a computer processor. The computing system further comprises a computer readable storage medium storing program instructions configured for execution by the computer processor in order to cause the computing system to access medical data associated with a plurality of patients, wherein the medical data comprises an ailment identified as affecting the respective patient. The computer readable storage medium further stores program instructions configured for execution by the computer processor in order to access a plurality of medical claims, wherein each medical claim corresponds to at least one of the plurality of patients and is associated with one of a plurality of healthcare providers. The computer readable storage medium further stores program instructions configured for execution by the computer processor in order to determine a first set of medical claims in the plurality of medical claims that comprise claims for reimbursement for treatments of ailments not identified as affecting the respective patient. The computer readable storage medium further stores program instructions configured for execution by the computer processor in order to generate a user interface comprising a provider window depicting a selectable list of one or more of the plurality of healthcare providers, and a claim adjustment window. The user interface may be configured to receive a selection of a first healthcare provider in the list of healthcare providers and, in response to selection of the first healthcare provider, display, in the claim adjustment window, one or more medical claims in the first set of medical claims that are each associated with the first healthcare provider.

The computing system of the preceding paragraph can have any sub-combination of the following features: the user interface further comprises a gaps in care window; where the program instructions are further configured to cause the computing system to determine a first set of patients in the plurality of patients that have not submitted, during a first period of time, a claim for reimbursement for a treatment of an ailment identified as affecting the respective patient, where the user interface is further configured to display, in the gaps in care window for each user in the first set of patients that is associated with the first healthcare provider, a notification to contact the respective patient; the user interface is further configured to display, in the provider window, a plurality of histograms, and where each histogram is associated with a healthcare provider in the plurality of healthcare providers; each histogram is configured to indicate a number of medical claims in the first set of medical claims that are associated with the respective provider when the claim adjustment window is selected; each histogram is configured to indicate a number of patients in the first set of patients that are associated with the respective provider when the gaps in care window is selected; each histogram comprises information displayed using a logarithmic scale; where the program instructions are further configured to cause the computing system to receive a selection of a first notification to contact a first patient in the first set of patients, where the user interface is configured to display, in the gaps in care window, a schedule window that overlaps at least a portion of the first notification, where the schedule window comprises an option to indicate that an appointment has been scheduled with the first patient and an option to indicate that the appointment with the first patient has been completed; the gaps in care window comprises a new window and a scheduled appointment window, where the new window comprises the first notification, and where the user interface is further configured to display, in the scheduled appointment window and not the new window, the first notification in connection with a selection of the option to indicate that the appointment has been scheduled with the first patient; the gaps in care window comprises a first notification to contact a first patient in the first set of patients and a notification number associated with the first notification that indicates a number of reasons to contact the first patients; the user interface is further configured to display, in the gaps in care window, a second notification to contact the first patient and a third notification to contact the first patient in connection with a selection of the first notification; and the user interface comprises a sort button, and where the sort button, when selected, causes the claim adjustment window to display the one or more medical claims in the first set of medical claims in one of an alphabetical order, an order based on date, or an order based on importance of the respective medical claim.

Another aspect of the disclosure provides a computer-implemented method of processing a large amount of dynamically updating data. The computer-implemented method comprises, as implemented by one or more computer systems comprising computer hardware and memory, the one or more computer systems configured with specific executable instructions, accessing medical data associated with a plurality of users, wherein the medical data comprises an ailment identified as affecting the respective user. The computer-implemented method further comprises accessing a plurality of user claims, wherein each user claim corresponds to at least one of the plurality of users and is associated with one of a plurality of healthcare providers. The computer-implemented method further comprises determining, based on the accessed medical data, a first set of users claims in the plurality of user claims that comprise claims for reimbursement for treatments of ailments not identified as affecting the respective user. The computer-implemented method further comprises generating a user interface comprising a provider window depicting a selectable list of one or more of the plurality of healthcare providers, and a claim adjustment window. The computer-implemented method further comprises receiving a selection of a first healthcare provider in the list of healthcare providers. In response to selection of the first healthcare provider, the computer-implemented method further comprises updating the claim adjustment window of the user interface to include one or more user claims in the first set of user claims that are each associated with the first healthcare provider.

The computer-implemented method of the preceding paragraph can have any sub-combination of the following features: the user interface further comprises a gaps in care window; where the computer-implemented method further comprises determining a first set of users in the plurality of users that have not submitted, during a first period of time, a claim for reimbursement for a treatment of an ailment identified as affecting the respective user, and updating the gaps in care window, for each user in the first set of users that is associated with the first healthcare provider, to include a notification to contact the respective user; and where the computer-implemented method further comprises updating the provider window to include a plurality of histograms, wherein each histogram is associated with a healthcare provider in the plurality of healthcare providers.

Another aspect of the disclosure provides a non-transitory computer-readable medium comprising one or more program instructions recorded thereon, the instructions configured for execution by a computing system comprising one or more processors in order to cause the computing system to access medical data associated with a plurality of users, wherein the medical data comprises an ailment identified as affecting the respective user. The computer-readable medium further comprises one or more program instructions configured for execution in order to cause the computing system to access a plurality of user claims, wherein each user claim corresponds to at least one of the plurality of users and is associated with one of a plurality of healthcare providers. The computer-readable medium further comprises one or more program instructions configured for execution in order to cause the computing system to determine a first set of users claims in the plurality of user claims that comprise claims for reimbursement for treatments of ailments not identified as affecting the respective user. The computer-readable medium further comprises one or more program instructions configured for execution in order to cause the computing system to generate a user interface comprising a selectable list of one or more of the plurality of healthcare providers. The computer-readable medium further comprises one or more program instructions configured for execution in order to cause the computing system to receive a selection of a first healthcare provider in the list of healthcare providers. The computer-readable medium further comprises one or more program instructions configured for execution in order to cause the computing system to, in response to selection of the first healthcare provider, update the user interface to include one or more user claims in the first set of user claims that are each associated with the first healthcare provider.

The non-transitory computer-readable medium of the preceding paragraph can have any sub-combination of the following features: where the instructions are further configured to cause the computing system to determine a first set of users in the plurality of users that have not submitted, during a first period of time, a claim for reimbursement for a treatment of an ailment identified as affecting the respective user, and update the user interface, for each user in the first set of users that is associated with the first healthcare provider, to include a notification to contact the respective user; where the instructions are further configured to cause the computing system to update the user interface to include a plurality of histograms, and where each histogram is associated with a healthcare provider in the plurality of healthcare providers; and each histogram is configured to indicate a number of user claims in the first set of user claims that are associated with the respective provider.

BRIEF DESCRIPTION OF THE DRAWINGS

FIG. 2 illustrates a user interface displaying claims adjustments for review.

FIGS. 5A-5K illustrate user interfaces displaying the selection, scheduling, and completion of a gaps in care item.

FIGS. 6A-6B illustrate user interfaces displaying the expansion of gaps in care items that have been combined for a single patient.

FIGS. 7A-7B illustrate user interfaces displaying the expansion of scheduled and unscheduled gaps in care items that have been combined for a single patient.

FIG. 9 illustrates a computer system with which certain methods discussed herein may be implemented.

DETAILED DESCRIPTION OF SPECIFIC EMBODIMENTS

Overview

As described above, the Patient Protection and Affordable Care Act (PPACA) allows for insurers that can prove they are insuring a sicker population in comparison to other insurers to be eligible for transfer payments. Thus, insurers may have an incentive to ensure that their risk pool looks as unappealing as possible. In other words, insurers may have an incentive to make sure everyone with expensive chronic diseases or other ailments that are indicative of an unhealthy individual are properly accounted for.

In addition, as described above, every Medicare Advantage plan offered by insurers is given a rating according to a five-star quality rating system that has gained more importance under the PPACA. Thus, insurers may be looking to improve their plan ratings in order to receive the extra benefits provided by the PPACA.

Accordingly, disclosed herein are various systems and methods that allow insurers to collect and analyze medical and/or pharmaceutical claims such that the ailments of insured individuals can be properly accounted for and/or the star ratings for plans can be improved or at least maintained. For example, the various systems described herein may determine, based on received claims, patient diagnoses that are not accounted for by a health insurance company and display such information in a user interface. Thus, health insurance company personnel may be able to visually identify such discrepancies and update the health insurance company records accordingly. As another example, the various systems described herein may identify patients that have not submitted claims for documented ailments or conditions. Such information may be displayed in a user interface as well. Thus, health insurance company personnel may be able to identify patients who may not be seeking treatment (or may have failed to report that treatments were acquired) and contact such patients to schedule appointments, thereby working to improve and/or maintain a plan's star rating.

Claim Collection and Analysis System Overview

Figure 1:
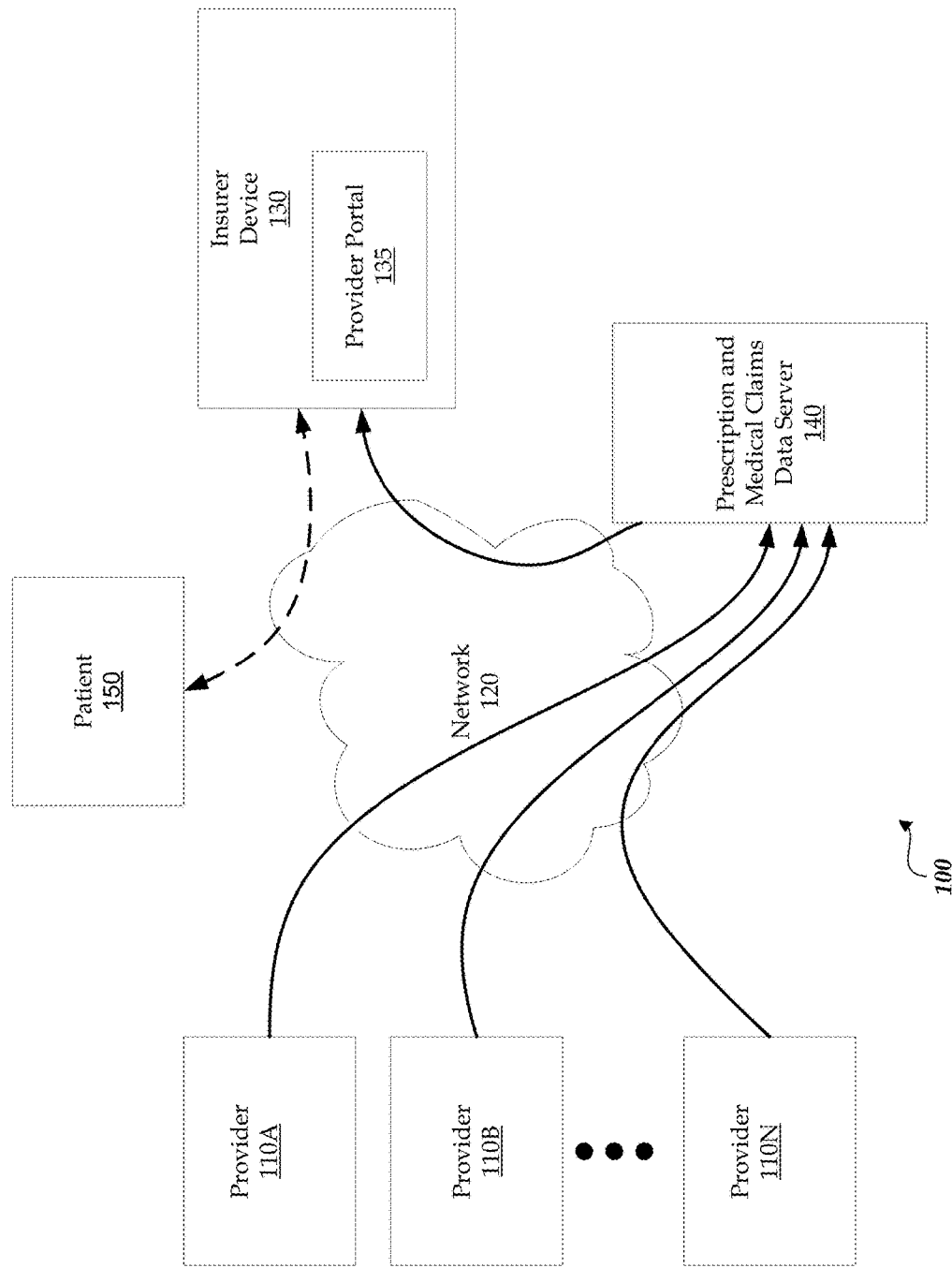
FIG. 1 illustrates a block diagram of a system for collecting and analyzing claims.

FIG. 1 illustrates a block diagram of a system 100 for collecting and analyzing claims. The system 100 comprises one or more providers 110, an insurer device 130, a provider portal 135, a prescription and medical claims data sever 140, a patient 150, and a network 120.

In the embodiment illustrated in FIG. 1, the one or more providers 110 (e.g., doctors, hospitals, pharmacies, etc.), which may be implemented by one or more first physical computing devices, are communicatively connected to the prescription and medical claims data server 140, which may be implemented by one or more second physical computing devices, over the network 120. Similarly, the insurer device 130 (e.g., operated by an insurance company, such as Blue Cross, Health Net, or Kaiser Permanente) may be implemented by one or more third physical computing devices and may be communicatively connected to the prescription and medical claims data server 140 over the network 120. The prescription and medical claims data server 140 can be operated by the insurance company or can be operated by a third party (e.g., a company that contracts with an insurance company, a healthcare provider, etc.). The patient 150, which may be implemented by one or more fourth physical computing devices, may likewise be communicatively connected to the insurer device 130 over the network 120. In some embodiments, each such physical computing device may be implemented as a computer system including some or all of the components illustrated in the example computing system 900 of FIG. 9. For example, the one or more providers 110, the insurer device 130, the prescription and medical claims data server 140, and/or the patient 150 may be implemented in a computer system as a set of program instructions recorded on a machine-readable storage medium.

The one or more providers 110 represent devices operated by healthcare providers (e.g., doctors, hospitals, pharmacies, etc.). Healthcare personnel (e.g., doctors, nurses, pharmacists, hospital or clinic staff, etc.) may submit medical and/or pharmaceutical claims to insurance companies (e.g., health insurance companies) on behalf of patients. Medical claims may include claims that are submitted to insurance companies to receive payment for medical services administered by the healthcare provider. Likewise, pharmaceutical claims may include claims that are submitted to insurance companies to receive payment for drugs distributed by the healthcare provider. These claims may be transmitted to the prescription and medical claims data server 140 for storage and/or for access by the insurer device 130. In some embodiments, information related to patient ailments entered into electronic medical record (EMR) systems (e.g., referred to herein as "EMR data") may also be transmitted to the prescription and medical claims data server 140 for storage and used in a manner as described herein with the medical and/or pharmaceutical claims. In some embodiments, lab claims and/or lab results may also be transmitted to the prescription and medical claims data server 140 for storage and used in a manner as described herein with the medical and/or pharmaceutical claims.

The insurer device 130 represents a device operated by a health insurance company that allows insurance company personnel to analyze pharmaceutical and/or medical claims received from the prescription and medical claims data server 140 and identify expected pharmaceutical and/or medical claims that were not received, for example. In an embodiment, the insurer device comprises a provider portal 135, which allows insurance company personnel to analyze claims, manipulate claims, identify claims that were not received, and/or contact patients via a graphical user interface (GUI). For example, the provider portal 135 may include GUI logic. The GUI logic may be a set of program instructions configured for execution by one or more computer processors of the insurer device 130, which are operable to receive user input and to display a graphical representation of claims using the approaches described herein. The GUI logic may be operable to receive user input from, and display a graphical representation of the claims, in a GUI that is provided on a display (not shown) of the insurer device 130 and/or another computing device that is in communication with the provider portal 135.

The prescription and medical claims data server 140 may be implemented as a special-purpose computer system having logical elements. In an embodiment, the logical elements may comprise program instructions recorded on one or more machine-readable storage media. Alternatively, the logical elements may be implemented in hardware, firmware, or a combination thereof.

When executed by one or more processors of the computer system, logic in the prescription and medical claims data server 140 is operable to receive, store, analyze, and/or manipulate claims and/or identify claims that were not received according to the techniques described herein. For example, the prescription and medical claims data server 140 may comprise the provider portal 135 (not shown), which can then be accessed by another device, such as the insurer device 130, via a network interface (e.g., a browser). In one embodiment, the provider portal 135 and/or the prescription and medical claims data server 140 may be implemented in a Java Virtual Machine (JVM) that is executing in a distributed or non-distributed computer system. In other embodiments, the provider portal 135 and/or the prescription and medical claims data server 140 may be implemented as a combination of programming instructions written in any programming language (e.g. C++ or Visual Basic) and hardware components (e.g., memory, CPU time) that have been allocated for executing the program instructions.

In an embodiment, the network 120 includes any communications network, such as the Internet. The network 120 may be a wired network, a wireless network, or a combination of the two. For example, network 120 may be a local area network (LAN) and/or a wireless area network (WAN).

Claims Adjustments

FIG. 2 illustrates a user interface 200 displaying claims adjustments for review. As illustrated in FIG. 2, the interface 200 includes a first pane 210 and a second pane 212. The first pane 210 may include a list of tasks and a list of healthcare providers. For example, the tasks may include an inbox 214 and an archived box 216. The list of healthcare providers may include healthcare providers 218A-L. For illustrative purposes, the inbox 214 and the healthcare provider 218A are selected in the first pane 210. The second pane 212 may include a claims adjustments tab 220 and a gaps in care tab 222. For illustrative purposes, the claims adjustments tab 220 is selected. The user interface 200 may be generated and/or displayed by the provider portal 135 as described above.

In an embodiment, the claim adjustments tab 220 includes a list of claims adjustments. As used herein, claims adjustments comprise claims for reimbursement submitted on behalf of individuals that relate to treatments for ailments or conditions not identified by an insurance company as affecting the respective individual. For example, the prescription and medical claims data server 140 may receive claims for reimbursements submitted on behalf of patients. The prescription and medical claims data server 140 and/or a data store accessible by the insurer device 130 (not shown) may store a record of the ailments or conditions a patient has been diagnosed with. Such record may be maintained by the health insurance company. The prescription and medical claims data server 140 and/or the insurer device 130 may compare patient diagnoses with claims submitted on behalf of the respective patients. Any claims that do not correspond with a patient diagnosis may be flagged and provided to the provider portal 135.

The claim adjustments tab 220 may include pending claims adjustments (e.g., claims adjustments for which corresponding patient records have not yet been updated) when the inbox 214 is selected. The claims adjustments tab 220 may include completed claims adjustments (e.g., claims adjustments for which corresponding patient records have been updated) when the archived box 216 is selected. For example, the insurer device 130 can be used to update the record of the ailments or conditions a patient has been diagnosed with based on the claims adjustments such that the records are kept accurate. Pending claims adjustments may indicate that the record has not been updated and completed claims adjustments may indicate that the record has been updated. Thus, the claim adjustments tab 220 allows health insurance company personnel to view unreported diagnoses and update their records accordingly to increase the possibility of receiving transfer payments from other health insurance companies and/or other third parties.

The claims adjustments that are displayed in the user interface 200 may be organized by healthcare providers. For example, the claim adjustments displayed when the claims adjustments tab 220 is selected and when the healthcare provider 218A is selected may be for individuals that are patients of the healthcare provider 218A. The claim adjustments tab 220 may indicate a number of claim adjustments that are associated with the selected healthcare provider 218A-L.

Each claim adjustment may include a patient identification and claim information. For example, claim adjustment 230 includes a patient identification of "Patient #200016382" and claim information including a claim number (e.g., Claim #155385), a date the claim was made (e.g., Sep. 22, 2013), and claim notes (e.g., a diagnosis that is missing, the type of prescriptions used by the individual, when the prescriptions were used, etc.).

The inbox 214 may be associated with task number 215. The task number 215 may represent a total number of pending claims adjustments and a total number of pending gaps in care, which are described in greater detail below, for all individuals associated with the healthcare providers 218A-L.

The first pane 210 may further include a sort button 217. When selected, a user may be able to sort healthcare providers 218A by name, by location, by type of practice, by number of claims adjustments, by number of gaps in care, by risk posed by the healthcare provider (e.g., a larger number of claims adjustments and/or gaps in care may be riskier than a smaller number of the same), and/or the like.

Likewise, the second pane 212 may include a sort button 227. When selected, a user may be able to sort the claim adjustments listed in the claim adjustments tab 220 by patient name or number, by date, by type of ailment or condition, by importance, severity, or urgency (e.g., a missed diagnosis of cancer may be considered more important to record than a missed diagnosis of depression), and/or the like.

In an embodiment, the first pane 210 includes graphs, such as histograms or stacked bar graphs, associated with each of the healthcare providers 218A-L. For example, the healthcare provider 218L is associated with the graph 244. Each graph includes a first box that represents a number of pending claims adjustments and a second box that represents a number of pending gaps in care. For example, the graph 244 includes first box 240 and second box 242. The graphs may be based on a linear scale, a logarithmic scale, and/or the like. Each of the graphs may have the same and/or a different scale. Thus, the width of the first box and/or the second box may represent an absolute number of claims adjustments or gaps in care when compared to the widths of other first boxes and second boxes and/or may represent a relative number of claims adjustments to gaps in care with respect to the particular healthcare provider.

Figure 3A:
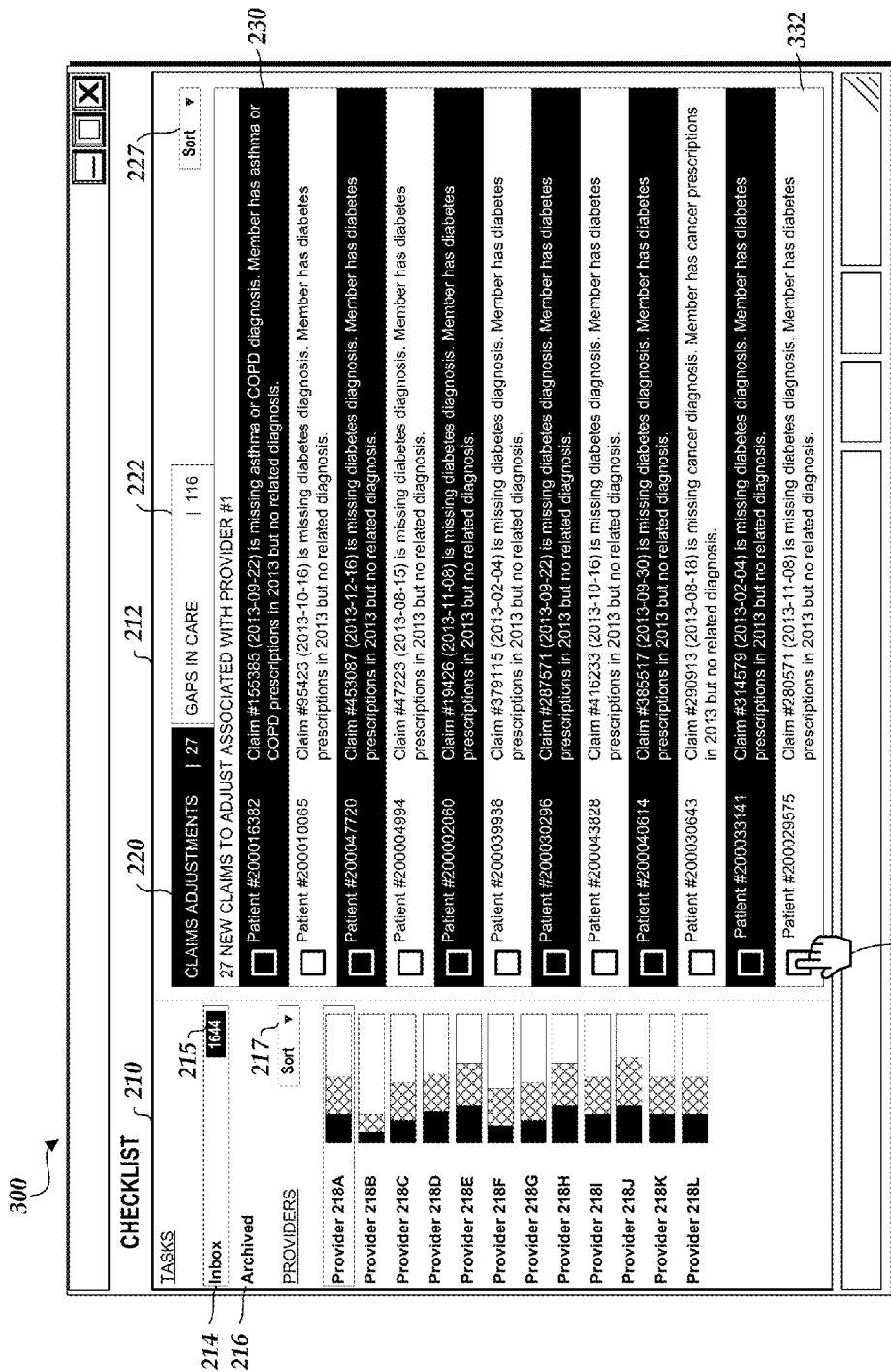
FIGS. 3A-C illustrate user interfaces displaying the selection and archiving of a pending claim adjustment.
Figure 3B:
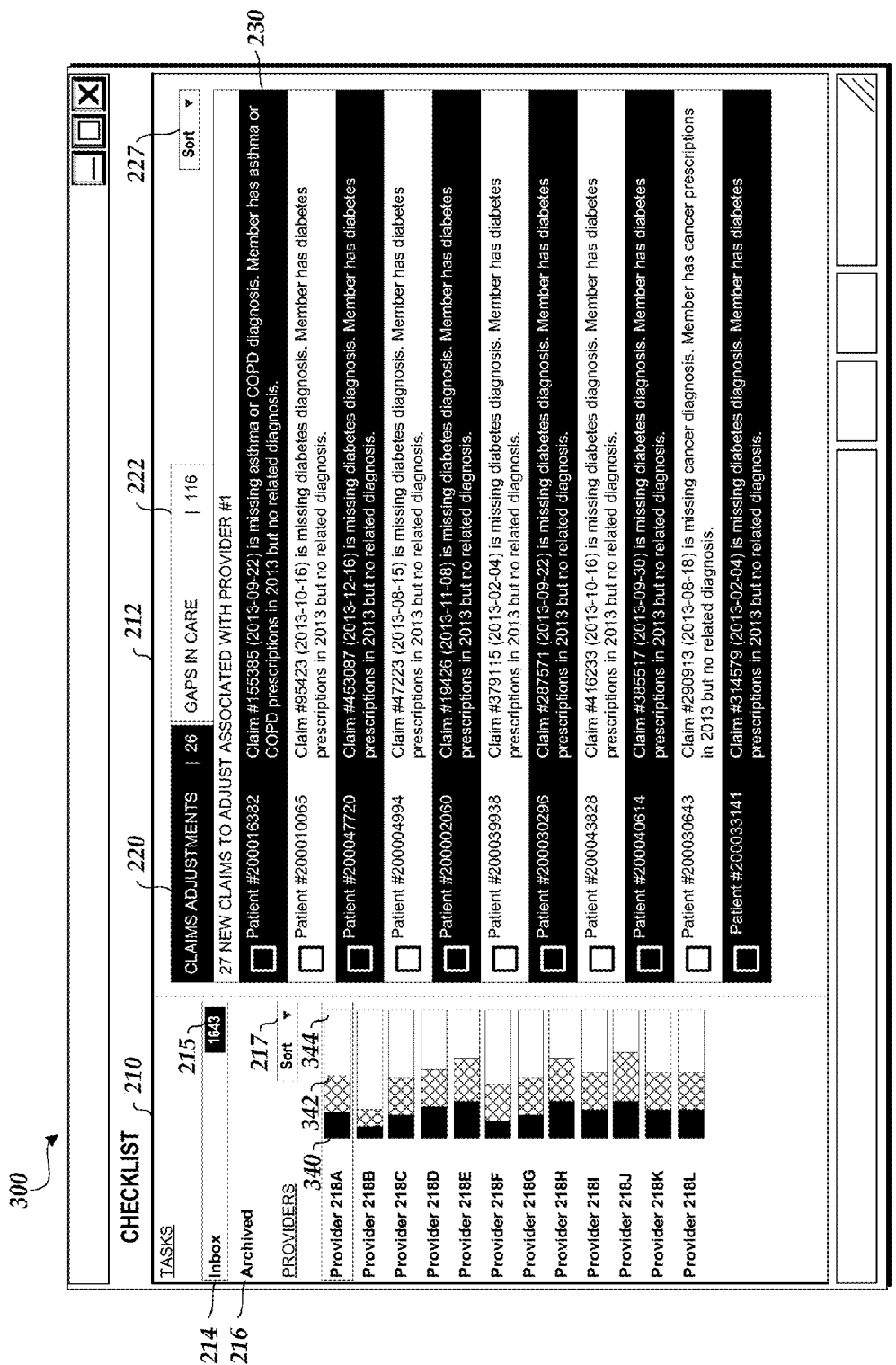
Figure 3C:
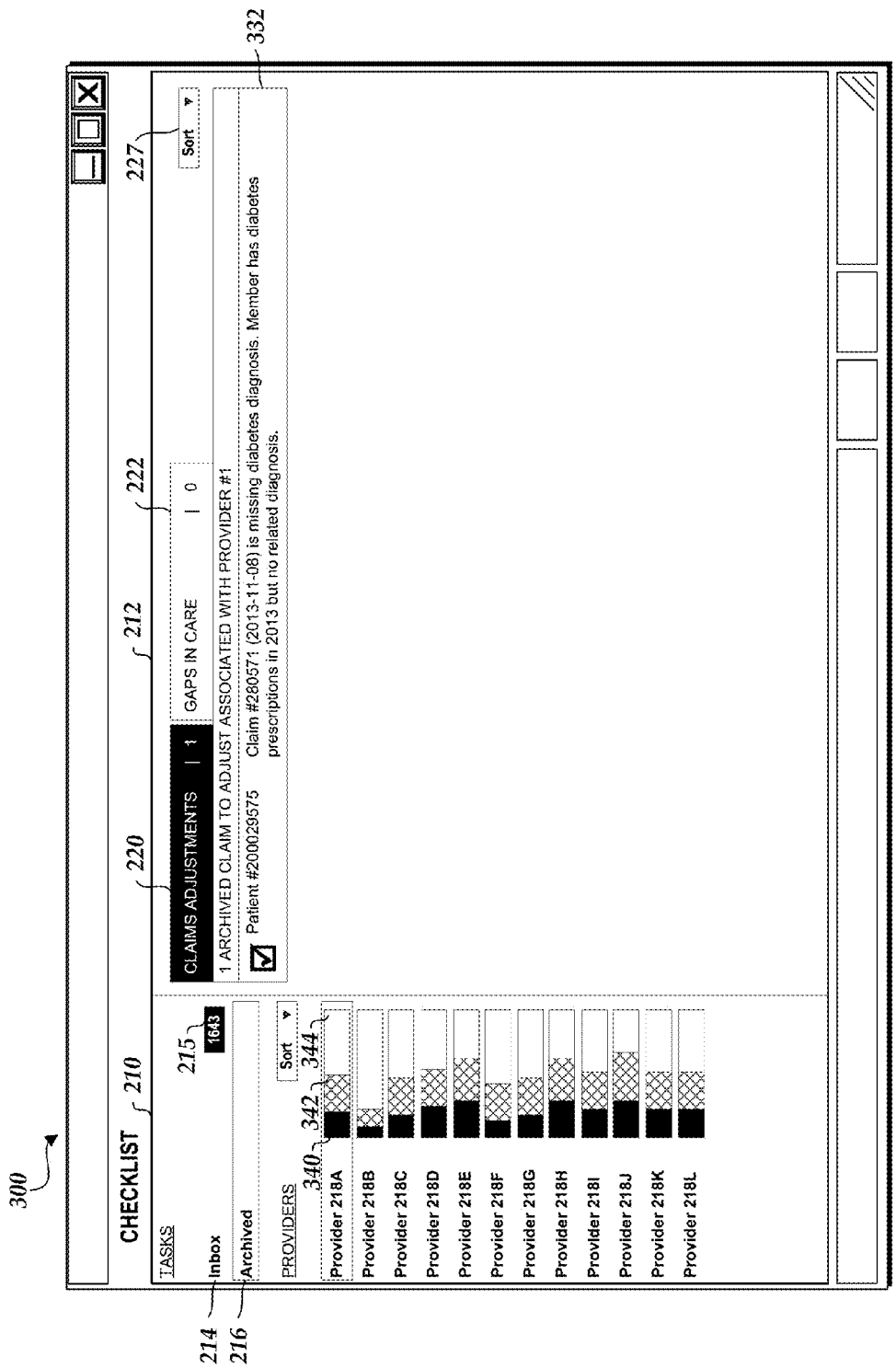

FIGS. 3A-C illustrate user interfaces 300 displaying the selection and archiving of a pending claim adjustment 332. As illustrated in FIG. 3A, a user on behalf of a health insurance company, using a cursor 350, may select the claim adjustment 332. For example, the user may select the claim adjustment 332 by placing the cursor 350 over a portion of the claim adjustment 332 (e.g., the box in the claim adjustment 332 next to the patient identification) and performing a selection operation (e.g., clicking a mouse button, tapping a touch interface, double-tapping a touch interface, etc.). The claim adjustment 332 may be selected by the user if the user has cleared the claim (e.g., updated the insurance company records such that the diagnosed ailment or condition of the patient is recorded accordingly). As illustrated in FIG. 3A, the cursor 350 is a mouse pointer, but may be any other indicia in other embodiments.

As illustrated in FIG. 3B, once the claim adjustment 332 is selected, the claim adjustment 332 disappears from the claim adjustments 220 tab. In addition, the task number 215 is reduced (e.g., from 1644 to 1643) and the number of claims adjustments listed in the claims adjustments tab 220 is reduced. Furthermore, in a graph 344 associated with the healthcare provider 218A, the width of a first box 340 may be reduced to reflect the reduced number of pending claims adjustments. The claim adjustment 332 is moved to the archived box, which is displayed when the archived box 216 is selected, as illustrated in FIG. 3C.

Figure 4:
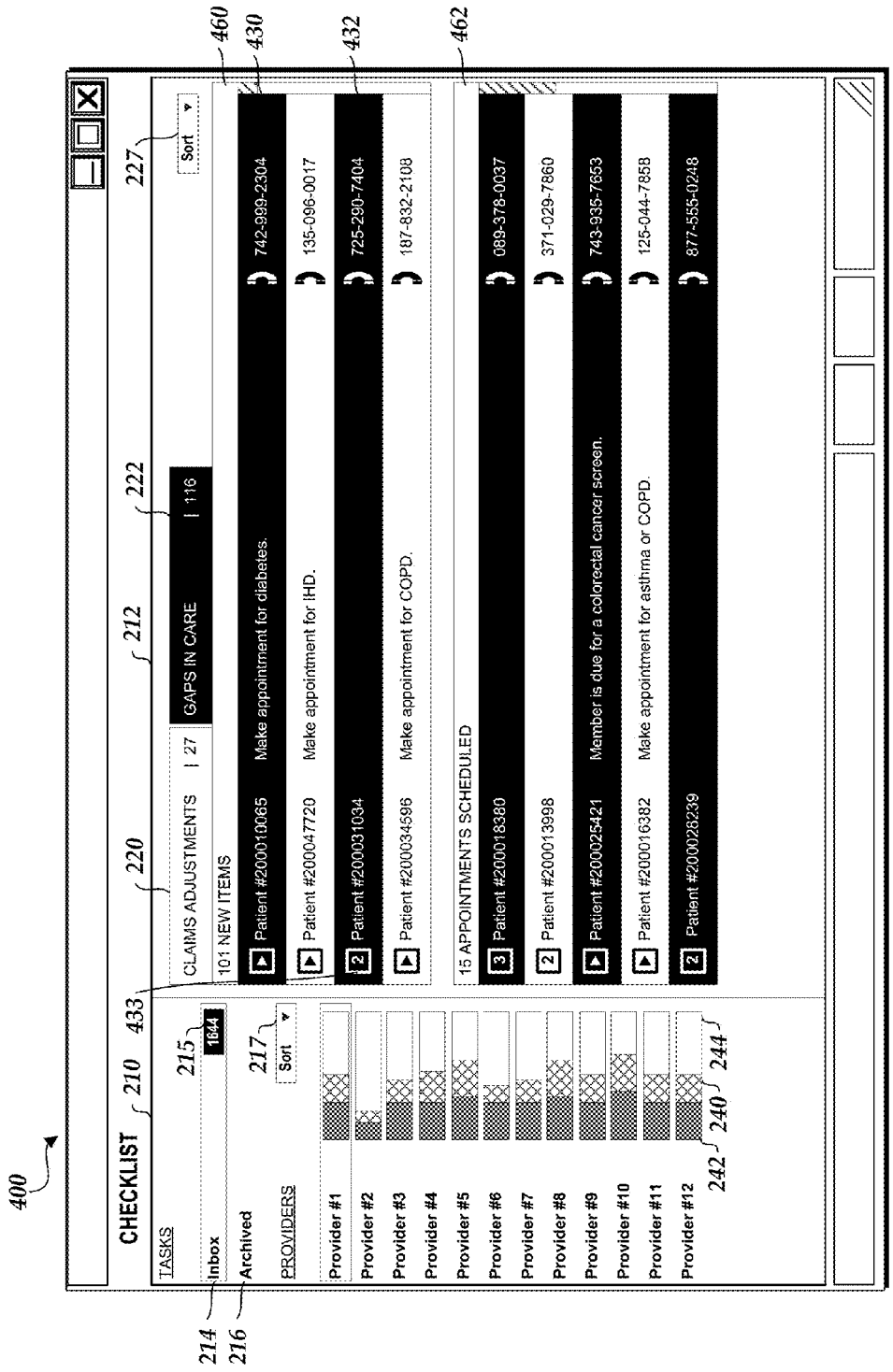
FIG. 4 illustrates a user interface displaying gaps in care for review.

FIG. 4 illustrates a user interface 400 displaying gaps in care for review. As illustrated in FIG. 4, the gaps in care tab 222 is selected. As used herein, gaps in care are items that indicate a patient or healthcare provider has not submitted a claim for reimbursement for a treatment of an ailment or condition identified as affecting the patient at some previous time. A gaps in care item may be generated if the claim has not been submitted within a certain period of time (e.g., a calendar year). For example, a patient may have been diagnosed with diabetes, yet the patient may not have scheduled an appointment to treat the condition during the calendar year. Thus, a gaps in care item may be generated for the patient. Generation of the gaps in care item may also depend on the eligibility of a patient (e.g., gender, age, etc.). As described above, the prescription and medical claims data server 140 and/or a data store accessible by the insurer device 130 (not shown) may store a record of the ailments or conditions a patient has been diagnosed with. Such data may be received directly from the providers 110. Such data may also be generated based on appointment information received and stored by the prescription and medical claims data server 140 and/or the data store accessible by the insurer device 130. The appointment information may include information relating to the last appointments scheduled (and attended) by the patient for a particular ailment or condition. The prescription and medical claims data server 140 and/or the insurer device 130 may compare patient diagnoses with claims submitted on behalf of the respective patients. If no claims correspond with a particular patient diagnosis, the lack of a claim for that patient may be flagged and provided to the provider portal 135.

In an embodiment, the gaps in care tab 222 includes a new items window 460 and a scheduled appointments window 462. The new items window 460 includes pending gaps in care items (e.g., gaps in care items for which appointments with patients have not been scheduled) and the scheduled appointments window 462 includes scheduled gaps in care items (e.g., gaps in care items for which appointments with patients have been scheduled).

A gaps in care item may include a patient identification, notes, and/or contact information for the patient. For example, the gaps in care item 430 includes a patient identification (e.g., Patient #200010065), notes (e.g., make appointment for diabetes), and a phone number for the patient. The contact information (e.g., the phone number) may be selected to connect the user with the patient, such as the patient 150 as illustrated in FIG. 1.

In some embodiments, there are multiple gaps in care items associated with a single patient. In such circumstances, the gaps in care items may be grouped together and such grouping may be indicated. For example, the gaps in care item 432 includes a box 433 with a number inside (e.g., 2). The number may represent a number of gaps in care items associated with the patient.

The graphs in the first pane 210 may transition from one view when the claims adjustments tab 220 is selected to a second view when the gaps in care tab 222 is selected. For example, the first box and the second box may switch places, visualized via a continuous animation. As illustrated in FIG. 4, the second box 242 and the first box 240 in the graph 244 have switched places.

Figure 5A:
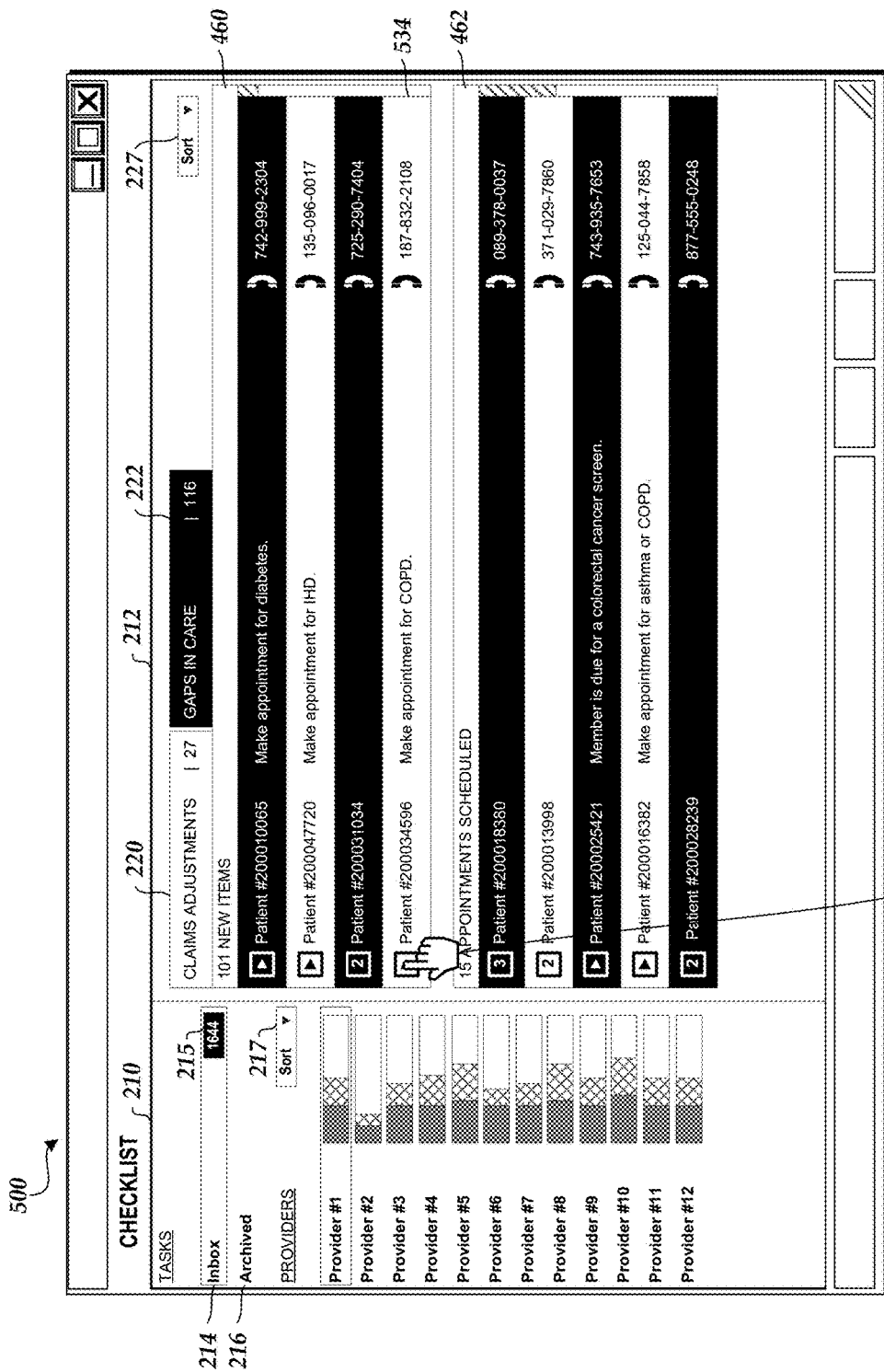

FIGS. 5A-5K illustrate user interfaces 500 displaying the selection, scheduling, and completion of a gaps in care item 534. As illustrated in FIG. 5A, a user on behalf of a health insurance company, using a cursor 550, may select the gaps in care item 534. When the sort button 227 is selected, a user may be able to sort the gaps in care items listed in the gaps in care tab 222 by patient name or number, by date, by type of ailment or condition, by importance, severity, or urgency (e.g., a missed appointment for cancer treatments may be considered more important to identify than a missed appointment for treatments for depression), and/or the like.

Figure 5C:
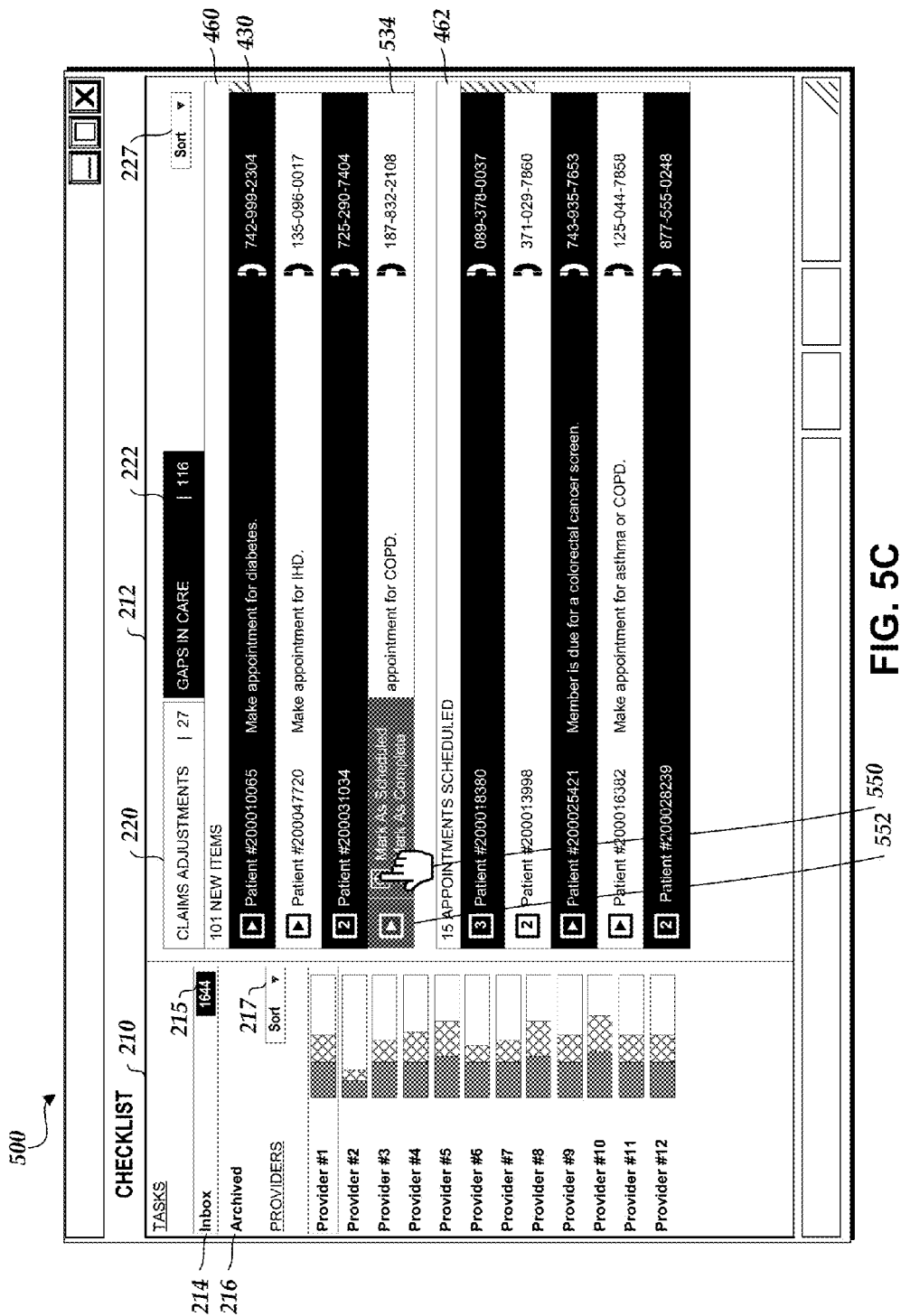

The gaps in care item 534 may be selected by the user if the user has contacted the patient to schedule an appointment and/or if the appointment has occurred, for example. As illustrated in FIG. 5B, a window 552 appears in the new items window 460 when a gaps in care item, such as the gaps in care item 534, is selected. The window 552 may comprise a "mark as scheduled" selection and a "mark as complete"

selection. As illustrated in FIG. 5C, the user using the cursor 550 may select either selection. If "mark as scheduled" is selected, the gaps in care item 534 is moved from the new items window 460 to the scheduled appointments window 462, as illustrated in FIG. 5D. Alternatively, if "mark as complete" is selected, the gaps in care item 534 is removed from the new items window 460 and is visible when the archived box 216 is selected (e.g., which displays gaps in care items that are completed), as illustrated in FIG. 5I.

Figure 5E:
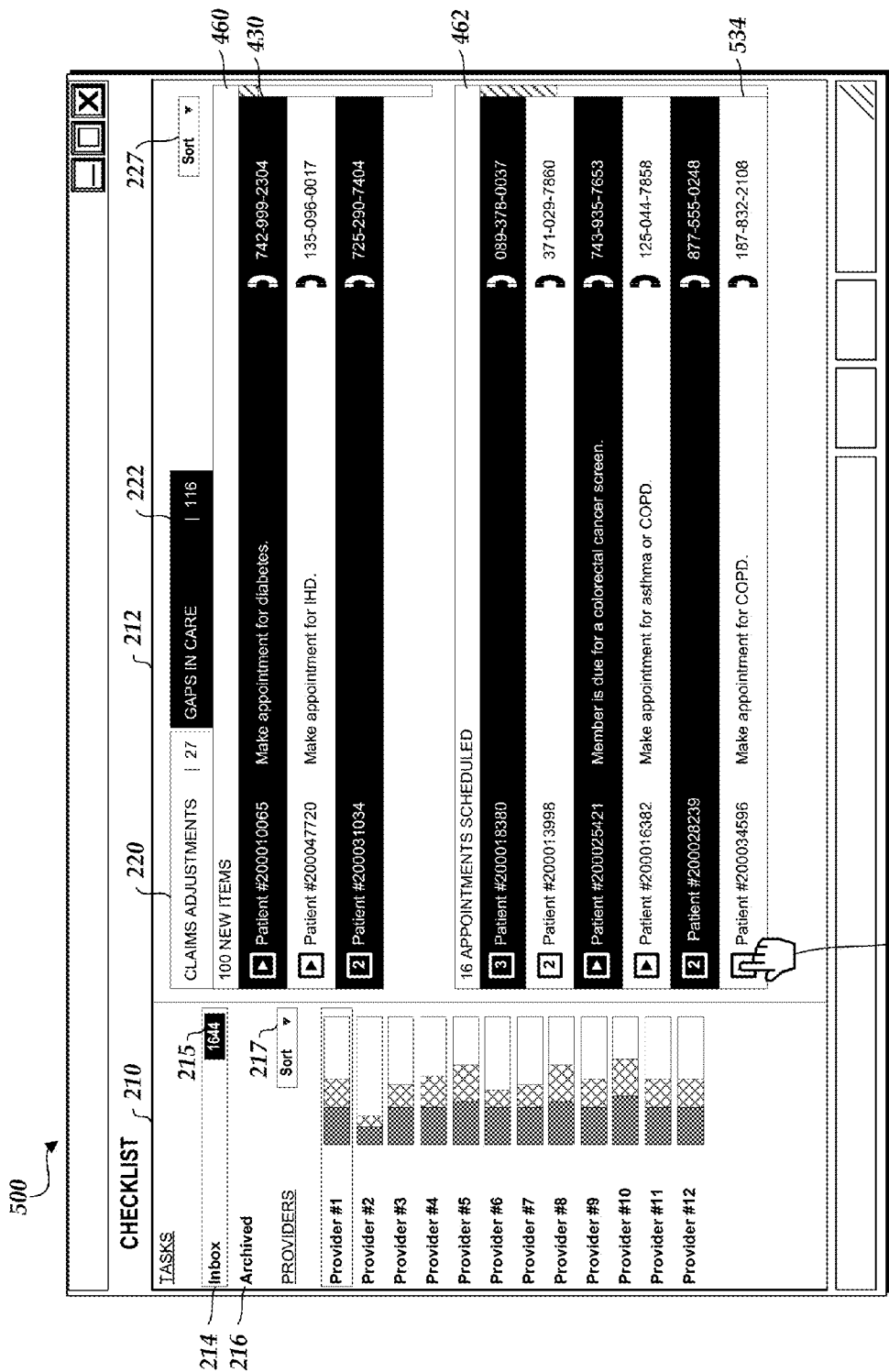
Figure 5F:
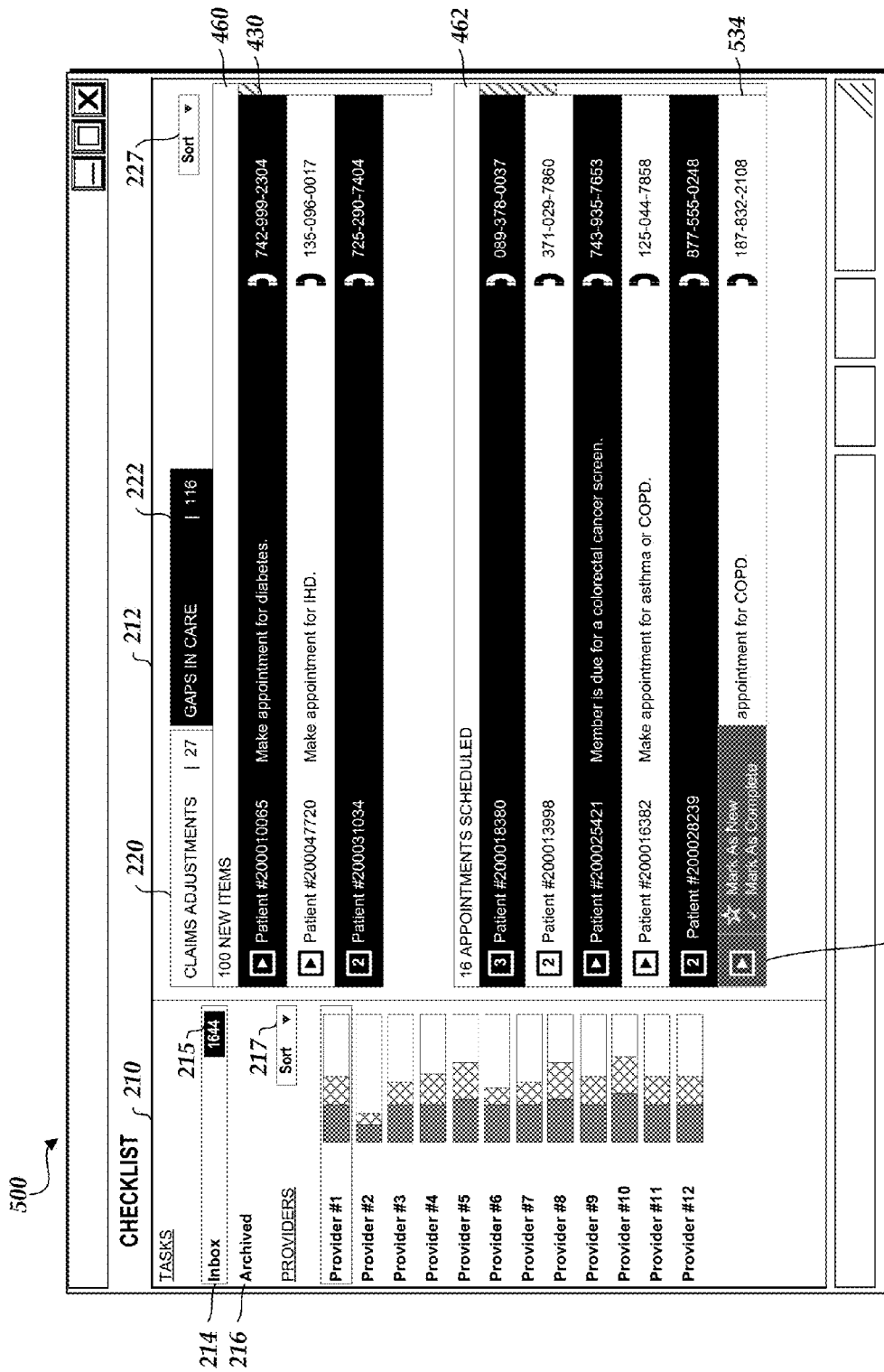
Figure 5G:
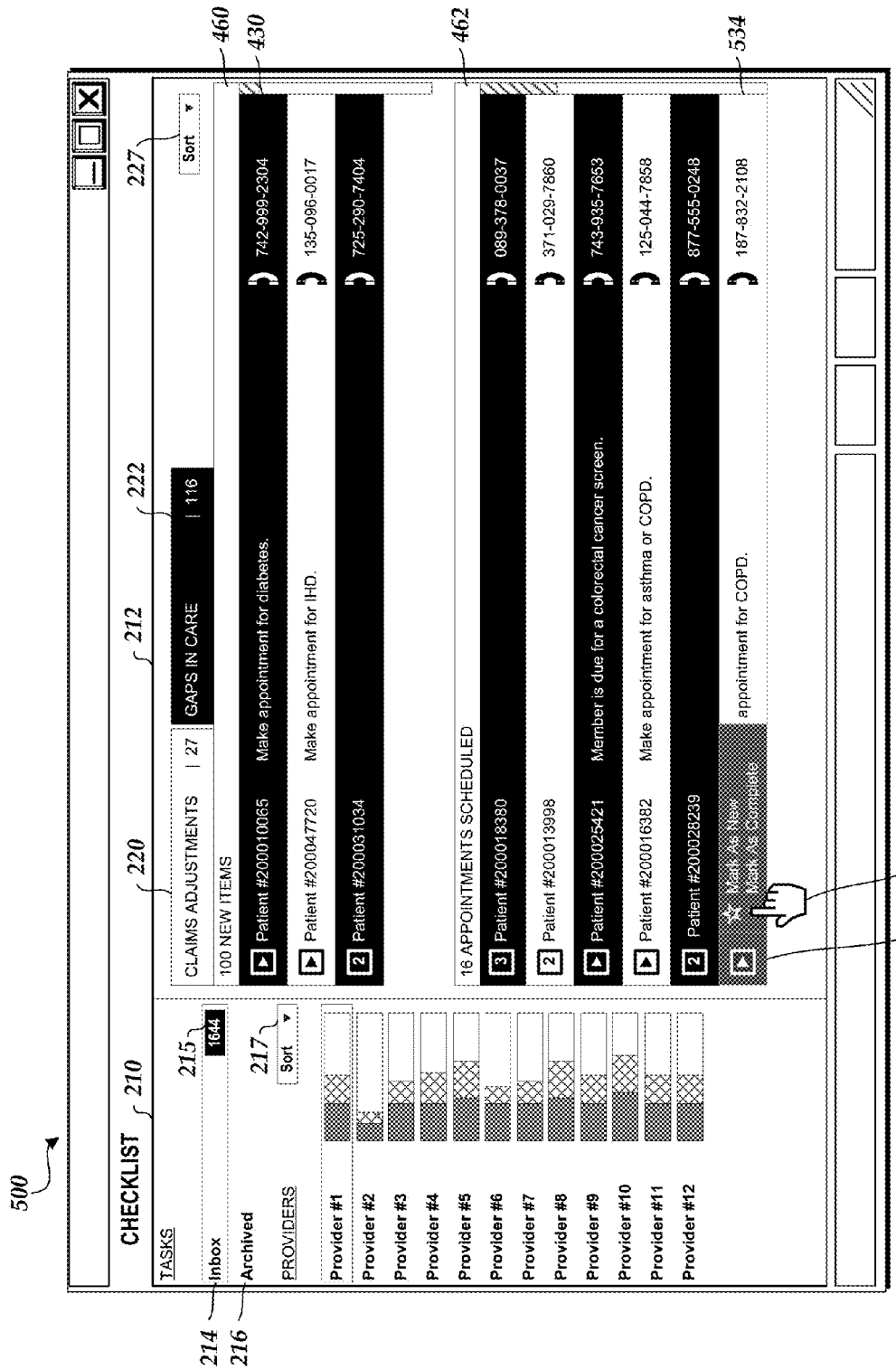

As illustrated in FIG. 5E, the user may select the gaps in care item 534 when it appears in the scheduled appointments window 462 using the cursor 550. Upon selecting a gaps in care item in the scheduled appointments window 462, such as the gaps in care item 534, a window 554 may appear in the scheduled appointments window 462, as illustrated in FIG. 5F. The window 554 may comprise a "mark as new" selection and a "mark as complete" selection. As illustrated in FIG. 5G, the user using the cursor 550 may select either selection. If "mark as new" is selected, the gaps in care item 534 is moved from the scheduled appointments window 462 to the new items window 460, as illustrated in FIG. 5A. Alternatively, if "mark as complete" is selected, the gaps in care item 534 is removed from the scheduled appointments window 462, as illustrated in FIG. 5H, and is visible when the archived box 216 is selected, as illustrated in FIG. 5I.

Figure 5H:
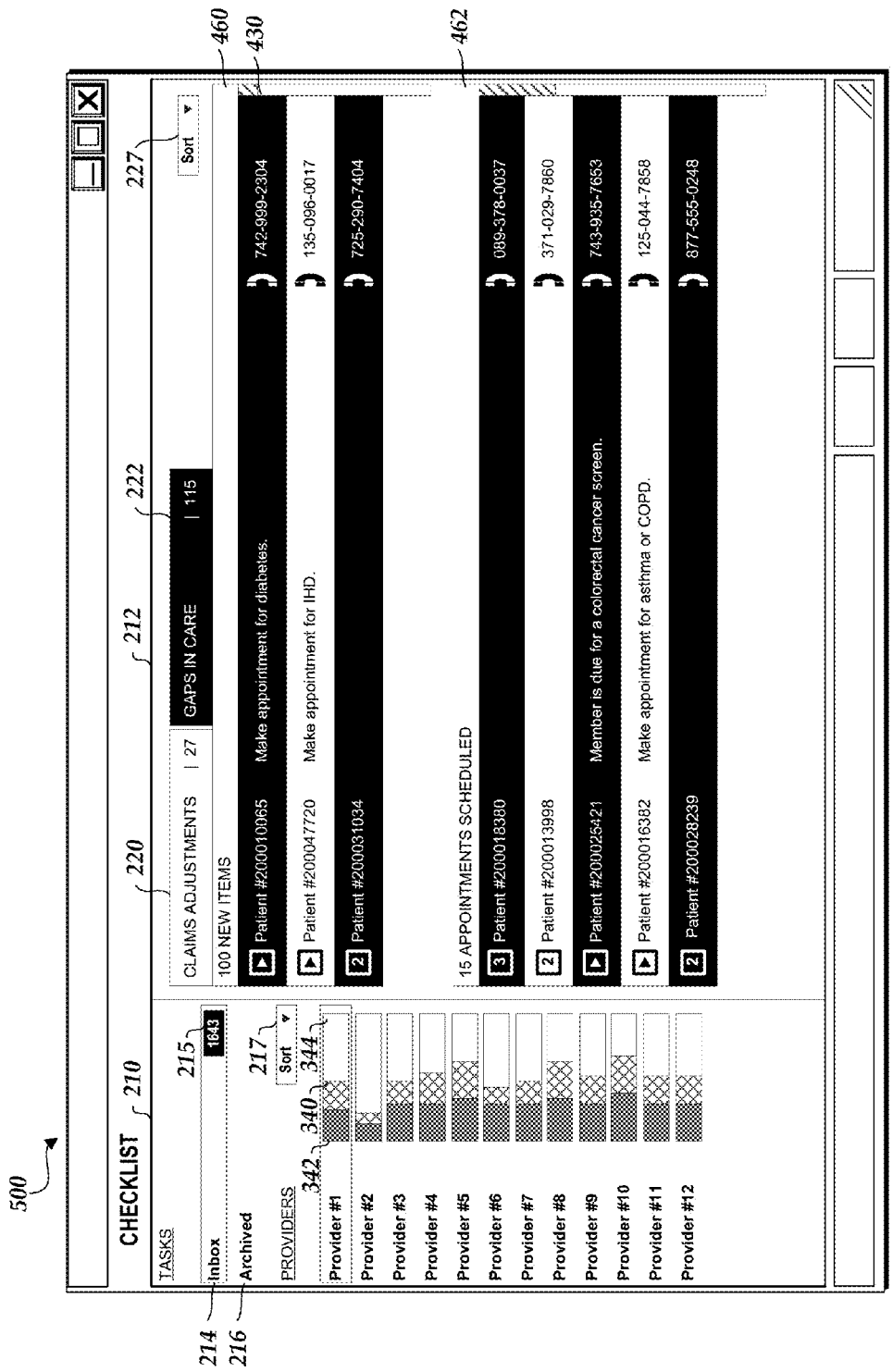

Furthermore, as illustrated in FIG. 5H, the task number 215 may decrease (e.g., from 1644 to 1643) once a gaps in care item, such as the gaps in care item 534, is marked as complete. In addition, the second box 342 may be adjusted (e.g., the width of the second box 342 may be reduced) to reflect the completion of a gaps in care item.

Figure 5I:
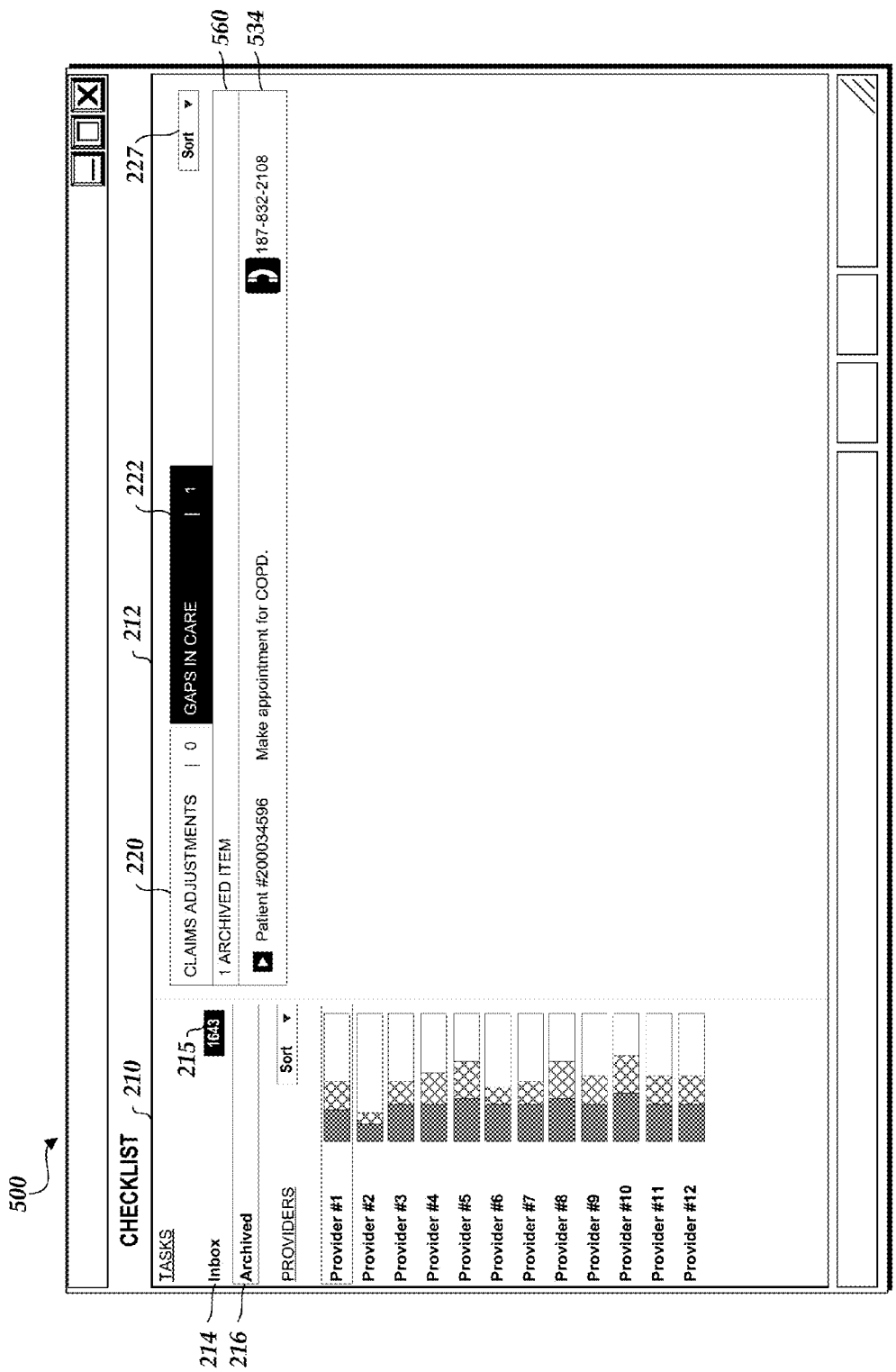
Figure 5J:
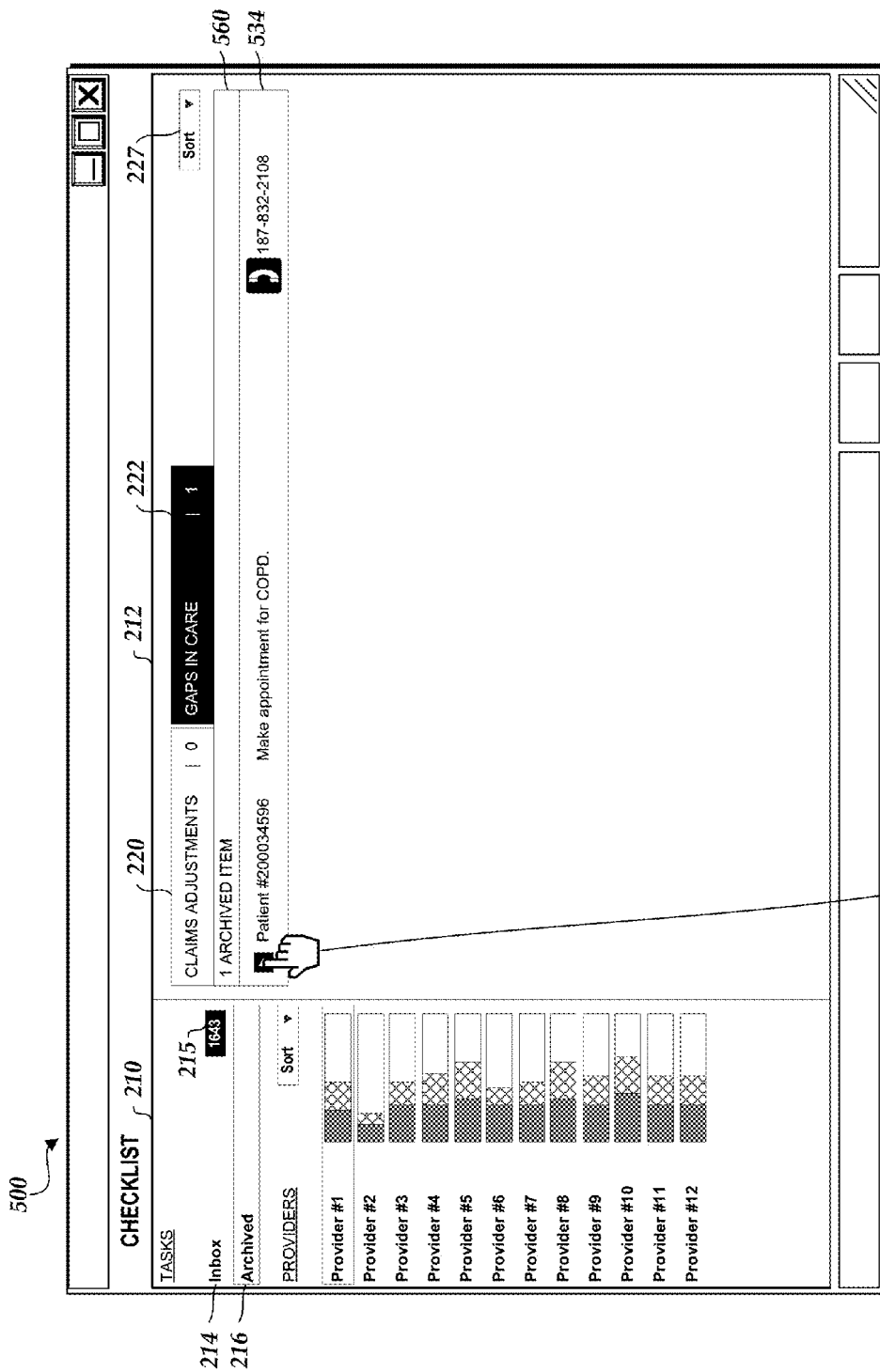

As illustrated in FIG. 5I, the user may select the archived box 216 to view completed gaps in care items. The completed gaps in care items may be displayed in an archived item window 560. As illustrated in FIG. 5J, the user may select the gaps in care item 534 using the cursor 550.

Figure 5K:
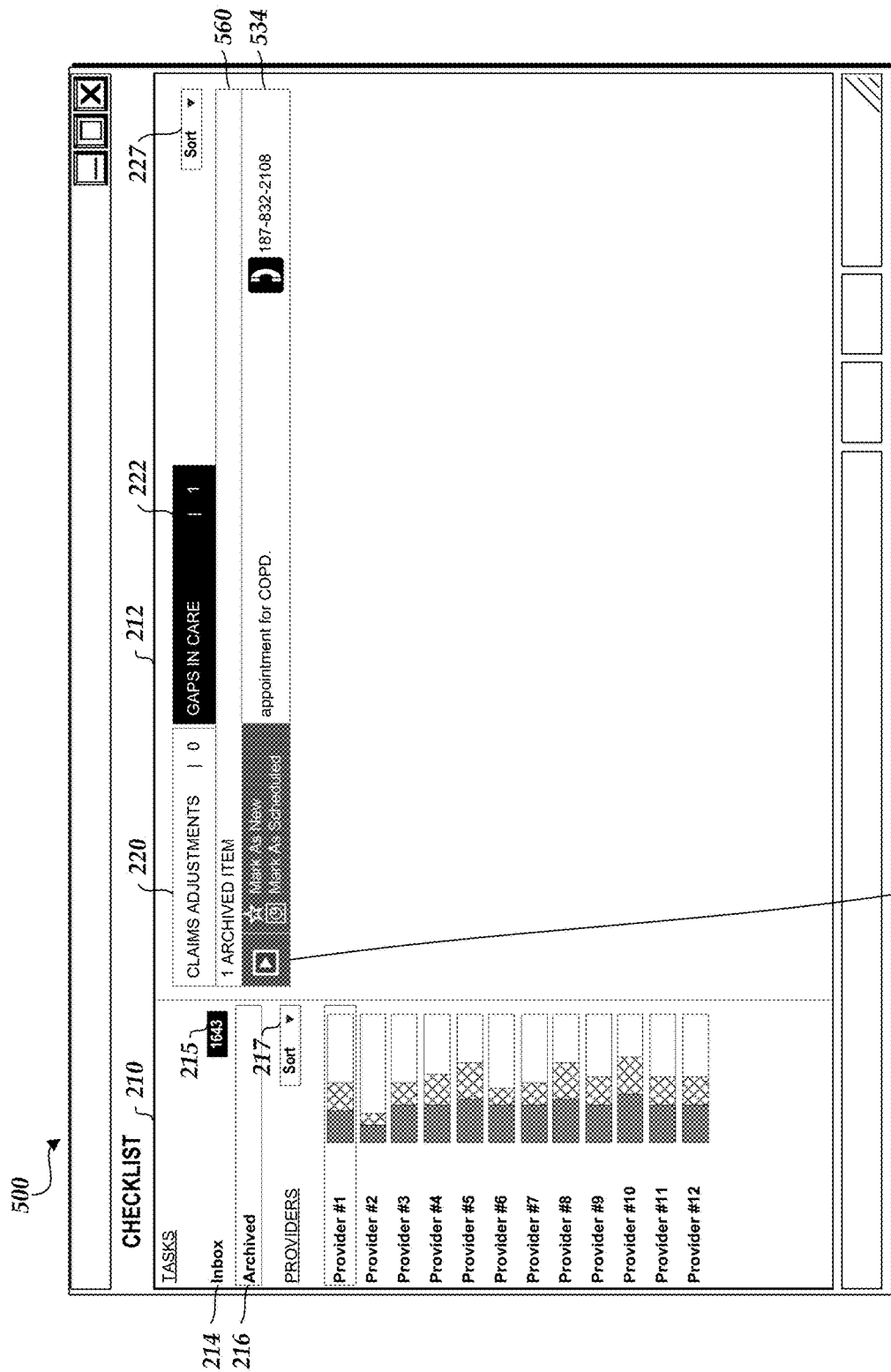

Upon selection of the gaps in care item 534, a window 556 may appear in the archived item window 560, as illustrated in FIG. 5K. The window 556 may comprise a "mark as new" selection and a "mark as scheduled" selection. If "mark as new" is selected, the gaps in care item 534 is moved from the archived item window 560 to the new items window 460, as illustrated in FIG. 5A. Alternatively, if "mark as scheduled" is selected, the gaps in care item 534 is moved from the archived item window 560 to the scheduled appointments window 462, as illustrated in FIG. 5D.

Figure 6A:
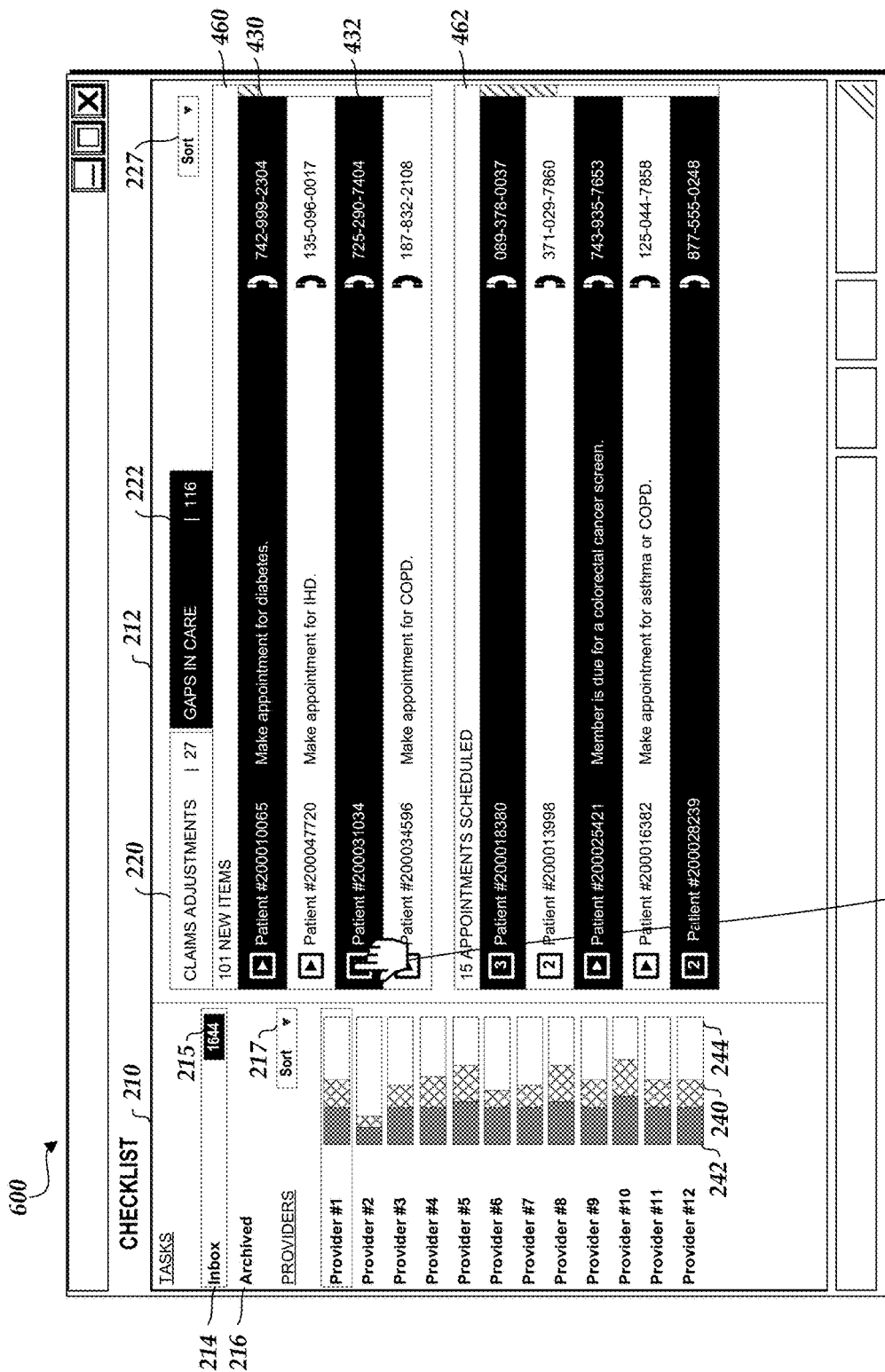

FIGS. 6A-6B illustrate user interfaces 600 displaying the expansion of gaps in care items that have been combined for a single patient. As illustrated in FIG. 6A, the user may select the gaps in care item 432, which is a gaps in care item that indicates multiple gaps in care items are associated with the patient, using a cursor 650. In an embodiment, upon selection of the gaps in care item 432, the gaps in care item 432 expands to show gaps in care items 632A-B, which are both associated with the same patient, as illustrated in FIG. 6B.

Figure 7A:
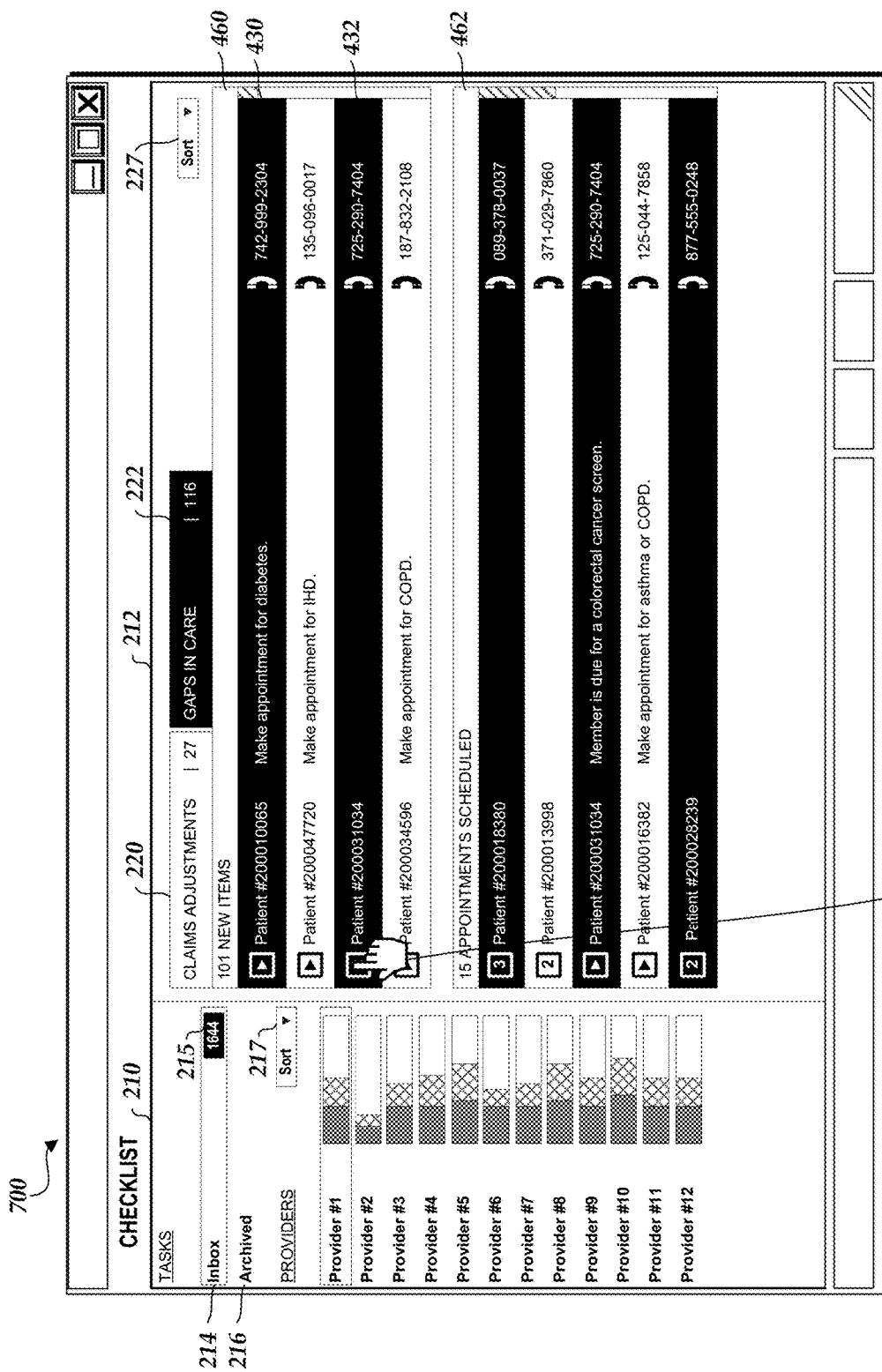

FIGS. 7A-7B illustrate user interfaces 700 displaying the expansion of scheduled and unscheduled gaps in care items that have been combined for a single patient. As illustrated in FIG. 7A, the user may select the gaps in care item 432 using a cursor 750. In an embodiment, upon selection of the gaps in care item 432, the gaps in care item 432 expands to show gaps in care items 732A-B, which are both associated with the same patient, as illustrated in FIG. 7B.

FIG. 7B further illustrates that the gaps in care item 732B has already been scheduled. The gaps in care item 732B is displayed in both the new items window 460 and the scheduled appointments window 462. For example, the gaps in care item 732B displayed in the new items window 460 includes a link (e.g., with the wording "SCHEDULED") to the same gaps in care item 732B displayed in the scheduled appointments window 462. The link, when selected, may provide information on a time and/or location when the appointment for the gaps in care item 732B has been scheduled. Thus, the user may readily access such information so that an appointment for the gaps in care item 732A may be scheduled near or at the same time and/or location as the appointment for the gaps in care item 732B.

Example Process Flow

Figure 8:
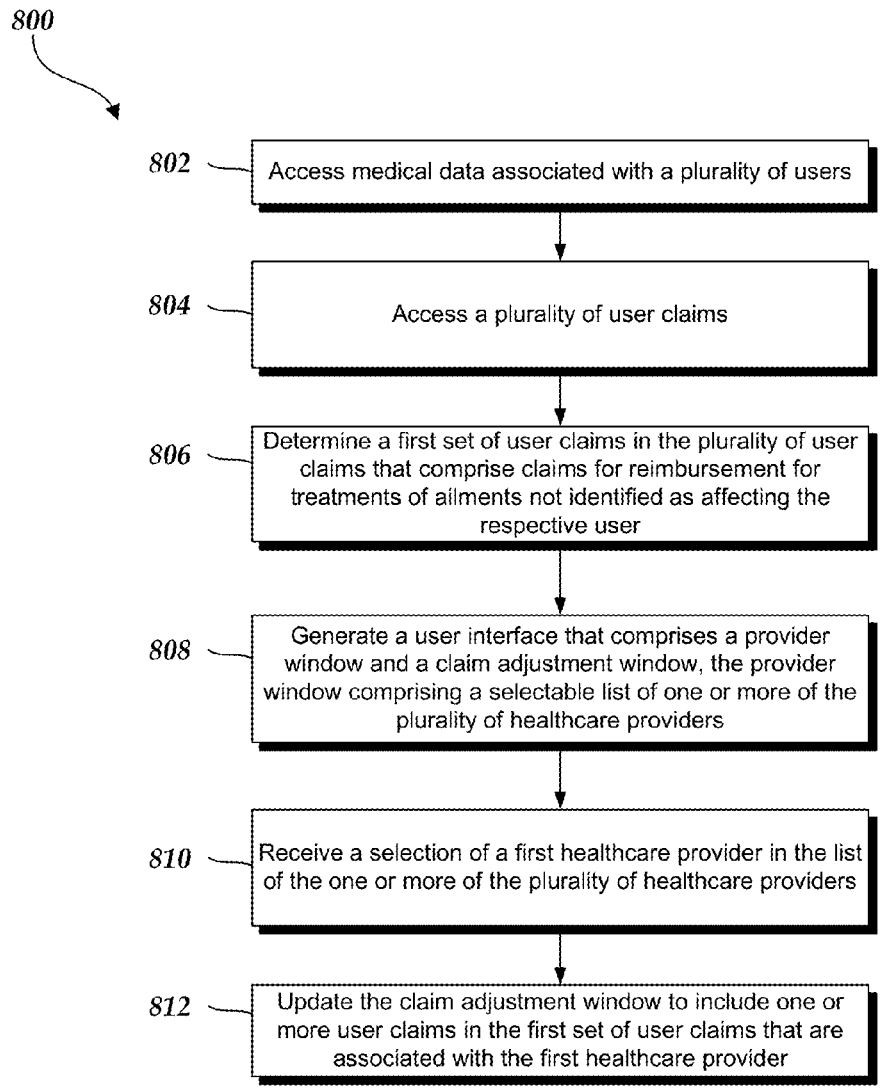
FIG. 8 is a flowchart depicting an illustrative operation of displaying claims adjustments.

FIG. 8 is a flowchart 800 depicting an illustrative operation of displaying claims adjustments. Depending on the embodiment, the method of FIG. 8 may be performed by various computing devices, such as by the insurer device 130 and/or the prescription and medical claims data server 140. For ease of discussion, the method is discussed herein with reference to insurer device 130 and the provider portal 135 of the insurer device 130. Depending on the embodiment, the method of FIG. 8 may include fewer and/or additional blocks and the blocks may be performed in an order different than illustrated.

In block 802, medical data associated with a plurality of users is accessed. For example, the medical data may include diagnosis data for a plurality of patients (e.g., ailments or conditions that a patient is diagnosed with). The medical data may be accessed from the providers 110 and/or the prescription and medical claims data server 140 and provided to the insurer device 130.

In block 804, a plurality of user claims are accessed. In an embodiment, the user claims are prescription claims and/or medical claims. In a further embodiment, the plurality of user claims are each associated with a healthcare provider in a plurality of healthcare providers.

In block 806, a first set of user claims in the plurality of user claims that comprise claims for reimbursement for treatments of ailments not identified as affecting the respective user is determined. In an embodiment, the determination is made based on comparing the received medical data with claims received on behalf of each respective patient.

In block 808, a user interface is generated that comprises a provider window and a claim adjustment window. In an embodiment, the provider window comprises a selectable list of one or more of the plurality of healthcare providers.

In block 810, a selection of a first healthcare provider in the list of the one or more of the plurality of healthcare providers is received. In block 812, the claim adjustment window is updated to include one or more user claims in the first set of user claims that are associated with the first healthcare provider.

Implementation Mechanisms

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

For example, FIG. 9 is a block diagram that illustrates a computer system 900 upon which an embodiment may be implemented. For example, any of the computing devices discussed herein, such as the insurer device 130, the prescription and medical claims data server 140, the providers 110, and the patient 150 may include some or all of the components and/or functionality of the computer system 900.

Computer system 900 includes a bus 902 or other communication mechanism for communicating information, and a hardware processor, or multiple processors, 904 coupled with bus 902 for processing information. Hardware processor(s) 904 may be, for example, one or more general purpose microprocessors.

Computer system 900 also includes a main memory 906, such as a random access memory (RAM), cache and/or other dynamic storage devices, coupled to bus 902 for storing information and instructions to be executed by processor 904. Main memory 906 also may be used for storing temporary variables or other intermediate information during execution of instructions to be executed by processor 904. Such instructions, when stored in storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or USB thumb drive (Flash drive), etc., is provided and coupled to bus 902 for storing information and instructions.

Computer system 900 may be coupled via bus 902 to a display 912, such as a cathode ray tube (CRT) or LCD display (or touch screen), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 804 and for controlling cursor movement on display 912. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 900 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor(s) 904 executing one or more sequences of one or more instructions contained in main memory 906. Such instructions may be read into main memory 906 from another storage medium, such as storage device 910. Execution of the sequences of instructions contained in main memory 906 causes processor(s) 904 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 910. Volatile media includes dynamic memory, such as main memory 906. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may retrieve and execute the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN (or WAN component to communicated with a WAN). Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

Terminology

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computing system configured to process a large amount of dynamically updating data, the computing system comprising:
    a network interface coupled to a data network for receiving and transmitting one or more packet flows;
    a display device;
    a computer processor;
    main memory; and
    a computer readable storage medium storing a plurality of program instructions configured for execution by the computer processor, wherein the plurality of program instructions are read into the main memory and accessed by the computer processor for execution in order to cause the computing system to:
        access medical data associated with a plurality of patients from a physical computing device associated with a medical facility over the data network;
        access a plurality of medical claims, wherein each medical claim corresponds to at least one of the plurality of patients and is associated with one of a plurality of healthcare providers;
        determine a first set of medical claims in the plurality of medical claims and a second set of medical claims in the plurality of medical claims;
        generate and display, on the display device, a user interface comprising a provider window and a claim adjustment window, wherein the provider window depicts a selectable list of one or more of the plurality of healthcare providers;
        receive a selection of a first healthcare provider in the list of healthcare providers; and
        in response to the selection of the first healthcare provider, read a first program instruction in the plurality of program instructions into the main memory for access by the computer processor, wherein execution of the first program instruction by the computer processor causes the display device to:
            display, in the claim adjustment window, one or more medical claims in the first set of medical claims that are each associated with the first healthcare provider,
            display, in the provider window, a plurality of stacked bar graphs associated with a corresponding plurality of healthcare providers, wherein a first stacked bar graph in the plurality of stacked bar graphs is associated with the first healthcare provider, wherein each stacked bar graph in the plurality of stacked bar graphs comprises a first box and a second box,
                wherein a width of the first box is based on a number of medical claims in the first set of medical claims associated with the respective healthcare provider, and
                wherein a width of the second box is based on a number of the medical claims in the second set of medical claims associated with the respective healthcare provider,
            receive an indication of a selection of a first medical claim in the one or more medical claims,
            in response to reception of the indication of the selection of the first medical claim,
                no longer display, in the claim adjustment window, the first medical claim, and
                cause the width of the first box of the first stacked bar graph to decrease from a first width to a second width less than the first width to reflect a reduced number of medical claims in the first set of medical claims that are associated with the first healthcare provider, and
            display an interactive element associated with a first patient in the plurality of patients, wherein the interactive element is configured to automatically initiate a communication between the computing system and a physical computing device associated with the first patient when selected.

2. The computing system of claim 1, wherein the program instructions are further configured to cause the computing system to determine a first set of patients in the plurality of patients that have not submitted, during a first period of time, a claim for reimbursement for a treatment of an ailment identified as affecting the respective patient, wherein the user interface is further configured to display, in a gaps in care window in the user interface for each user in the first set of patients that is associated with the first healthcare provider, a notification to contact the respective patient.

3. The computing system of claim 2, wherein the program instructions are further configured to cause the computing system to receive a selection of a first notification to contact the first patient in the first set of patients, wherein the user interface is further configured to display, in the gaps in care window, a schedule window that overlaps at least a portion of the first notification, wherein the schedule window comprises an option to indicate that an appointment has been scheduled with the first patient and an option to indicate that the appointment with the first patient has been completed.

4. The computing system of claim 3, wherein the gaps in care window comprises a new window and a scheduled appointment window, wherein the new window comprises the first notification, and wherein the user interface is further configured to display, in the scheduled appointment window and not the new window, the first notification in connection with a selection of the option to indicate that the appointment has been scheduled with the first patient.

5. The computing system of claim 2, wherein the gaps in care window comprises a first notification to contact the first patient in the first set of patients and a notification number associated with the first notification that indicates a number of reasons to contact the first patients.

6. The computing system of claim 5, wherein the user interface is further configured to display, in the gaps in care window, a second notification to contact the first patient and a third notification to contact the first patient in connection with a selection of the first notification.

7. The computing system of claim 1, wherein each stacked bar graph comprises information displayed using a logarithmic scale.

8. The computing system of claim 1, wherein the user interface comprises a sort button, and wherein the sort button, when selected, causes the claim adjustment window to display the one or more medical claims in the first set of medical claims in one of an alphabetical order, an order based on date, or an order based on importance of the respective medical claim.

9. The computing system of claim 1, wherein the plurality of program instructions are read into the main memory and accessed by the computer processor for execution in order to cause the computing system to, in response to a selection of the interactive element, read a second program instruction in the plurality of program instructions into the main memory for access by the computer processor, wherein execution of the second program instruction by the computer processor causes the network interface to initiate the communication between the computing system and the physical computing device associated with the first patient.

10. The computing system of claim 1, wherein medical claims in the first set of medical claims that are associated with a second patient comprise claims for reimbursement for treatment of a first ailment, and wherein the first ailment is not identified by an entity as affecting the second patient.

11. A computer-implemented method of processing a large amount of dynamically updating data, the computer-implemented method comprising:

as implemented by one or more computer systems comprising a computer processor, a display device, and main memory, the one or more computer systems configured with specific executable instructions,
accessing medical data associated with a plurality of users;
accessing a plurality of user claims, wherein each user claim corresponds to at least one of the plurality of users and is associated with one of a plurality of healthcare providers;
determining, based on the accessed medical data, a first set of user claims in the plurality of user claims and a second set of user claims in the plurality of user claims;
generating and displaying, on the display device, a user interface comprising a provider window and a claim adjustment window, wherein the provider window depicts a selectable list of one or more of the plurality of healthcare providers;
receiving a selection of a first healthcare provider in the list of healthcare providers; and
in response to the selection of the first healthcare provider, reading a first program instruction in the plurality of program instructions into the main memory for access by the computer processor, wherein execution of the first program instruction by the computer processor causes the display device to:
display, in the claim adjustment window of the user interface, one or more user claims in the first set of user claims that are each associated with the first healthcare provider,
display, in the provider window, a plurality of stacked bar graphs associated with a corresponding plurality of healthcare providers, wherein a first stacked bar graph in the plurality of stacked bar graphs is associated with the first healthcare provider, wherein each stacked bar graph in the plurality of stacked bar graphs comprises a first box and a second box,
wherein a width of the first box is based on a number of user claims in the first set of user claims associated with the respective healthcare provider, and
wherein a width of the second box is based on a number of the user claims in the second set of user claims associated with the respective healthcare provider,
receive an indication of a selection of a first medical claim in the one or more medical claims,
in response to reception of the indication of the selection of the first medical claim,
no longer display, in the claim adjustment window, the first medical claim, and
cause the width of the first box of the first stacked bar graph to decrease from a first width to a second width less than the first width to reflect a reduced number of medical claims in the first set of medical claims that are associated with the first healthcare provider, and
display an interactive element associated with a first patient in the plurality of patients, wherein the interactive element is configured to automatically initiate a communication between the computing system and a physical computing device associated with the first patient when selected.

12. The method of claim 11, further comprising:
determining a first set of users in the plurality of users that have not submitted, during a first period of time, a claim for reimbursement for a treatment of an ailment identified as affecting the respective user; and
updating a gaps in care window in the user interface, for each user in the first set of users that is associated with the first healthcare provider, to include a notification to contact the respective user.

13. The method of claim 11, wherein user claims in the first set of user claims that are associated with a second user comprise claims for reimbursement for treatment of a first ailment, and wherein the first ailment is not identified by an entity as affecting the second patient.

14. The method of claim 11, wherein each stacked bar graph comprises information displayed using a logarithmic scale.

15. The method of claim 11, further comprising receiving a selection of a first notification to contact the first user in the first set of patients, wherein the user interface is further configured to display a schedule window that overlaps at least a portion of the first notification, and wherein the user interface comprises an option to indicate that an appointment has been scheduled with the first user and an option to indicate that the appointment with the first user has been completed.

16. A non-transitory computer-readable medium comprising one or more program instructions recorded thereon, the instructions configured for execution by a computing system comprising one or more processors in order to cause the computing system to:
access medical data associated with a plurality of users;
access a plurality of user claims, wherein each user claim corresponds to at least one of the plurality of users and is associated with one of a plurality of healthcare providers;
determine a first set of users claims in the plurality of user claims and a second set of user claims in the plurality of user claims;
generate and display, on a display device, a user interface comprising a selectable list of one or more of the plurality of healthcare providers;
receive a selection of a first healthcare provider in the list of healthcare providers; and
in response to the selection of the first healthcare provider, read a first program instruction in the plurality of program instructions into main memory for access by the one or more processors, wherein execution of the first program instruction by the one or more processors causes the display device to:
display, in the user interface, one or more user claims in the first set of user claims that are each associated with the first healthcare provider, display, in the user interface, a plurality of stacked bar graphs associated with a corresponding plurality of healthcare providers, wherein a first stacked bar graph in the plurality of stacked bar graphs is associated with the first healthcare provider, wherein each stacked bar graph in the plurality of stacked bar graphs comprises a first box and a second box,
  wherein a width of the first box is based on a number of user claims in the first set of user claims associated with the respective healthcare provider, and
  wherein a width of the second box is based on a number of the user claims in the second set of user claims associated with the respective healthcare provider,
receive an indication of a selection of a first medical claim in the one or more medical claims,
in response to reception of the indication of the selection of the first medical claim,
  no longer display, in the claim adjustment window, the first medical claim, and
  cause the width of the first box of the first stacked bar graph to decrease from a first width to a second width less than the first width to reflect a reduced number of medical claims in the first set of medical claims that are associated with the first healthcare provider, and
  display an interactive element associated with a first patient in the plurality of patients, wherein the interactive element is configured to automatically initiate a communication between the computing system and a physical computing device associated with the first patient when selected.

17. The medium of claim 16, wherein the instructions are further configured to cause the computing system to:
  determine a first set of users in the plurality of users that have not submitted, during a first period of time, a claim for reimbursement for a treatment of an ailment identified as affecting the respective user; and
  update the user interface, for each user in the first set of users that is associated with the first healthcare provider, to include a notification to contact the respective user.

18. The medium of claim 16, wherein user claims in the first set of user claims that are associated with a second user comprise claims for reimbursement for treatment of a first ailment, and wherein the first ailment is not identified by an entity as affecting the second patient.

19. The medium of claim 16, wherein each stacked bar graph comprises information displayed using a logarithmic scale.

* * * * *